US008894933B2

(12) United States Patent
Cadio et al.

(10) Patent No.: US 8,894,933 B2
(45) Date of Patent: Nov. 25, 2014

(54) PORTABLE HANDHELD MEDICAL DIAGNOSTIC DEVICES

(75) Inventors: Michel A. Cadio, Carmel, IN (US); Robert G. Davies, Carmel, IN (US); James R. Kurtock, Fishers, IN (US); Paul S. Rutkowski, Carmel, IN (US); Michael J. Blackburn, Indianapolis, IN (US); Randy J. Gardner, Bloomington, IN (US); Stacia Davis, McCordsville, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 556 days.

(21) Appl. No.: 12/536,531

(22) Filed: Aug. 6, 2009

(65) Prior Publication Data

US 2011/0034786 A1 Feb. 10, 2011

(51) Int. Cl.

| | |
|---|---|
| ***G01N 33/00*** | (2006.01) |
| ***A61B 5/00*** | (2006.01) |
| ***G06F 3/0488*** | (2013.01) |
| ***A61B 5/145*** | (2006.01) |
| ***G01N 33/487*** | (2006.01) |

(52) U.S. Cl.

CPC .............. *A61B 5/742* (2013.01); *G06F 3/0488* (2013.01); *A61B 5/14532* (2013.01); *A61B 2560/04* (2013.01); *A61B 2562/0295* (2013.01); *G01N 33/48785* (2013.01)

USPC ....................................... 422/82.05; 422/68.1

(58) Field of Classification Search

CPC ................... A61B 2560/04; A61B 2562/0295; A61B 5/14532; A61B 5/742; G01N 33/48785

USPC .............................................. 422/82.05, 68.1

See application file for complete search history.

(56) References Cited

U.S. PATENT DOCUMENTS

| | | | | |
|---|---|---|---|---|
| 6,514,460 | B1 * | 2/2003 | Fendrock | 422/404 |
| 6,635,167 | B1 | 10/2003 | Batman et al. | |
| 2005/0149090 | A1 | 7/2005 | Morita et al. | |
| 2006/0229502 | A1 | 10/2006 | Pollock et al. | |
| 2009/0286211 | A1 * | 11/2009 | Eisenhardt et al. | 434/113 |
| 2010/0331650 | A1 * | 12/2010 | Batman et al. | 600/365 |

FOREIGN PATENT DOCUMENTS

| | | | |
|---|---|---|---|
| WO | 01/08551 | A2 | 2/2001 |
| WO | 2006072034 | A1 | 7/2006 |
| WO | 2010075157 | A1 | 7/2010 |

OTHER PUBLICATIONS

Partial International Search Report for PCT No. PCT/EP2010/004782 dated Nov. 22, 2010.

International Search Report of the EPO as ISA as it relates to PCT/EP2010/004782 mailed Apr. 12, 2011.

International Search Report and Written Opinion of the EPO mailed Apr. 12, 2011 as it relates to PCT/EP2010/004782 filed Aug. 4, 2010.

* cited by examiner

*Primary Examiner* — Sam P Siefke

(74) *Attorney, Agent, or Firm* — Roche Diagnostics Operations, Inc.

(57) ABSTRACT

A portable handheld medical diagnostic device includes a front housing and a rear housing opposite the front housing. The front housing and the rear housing form a protective enclosure. A main circuit board is located in the protective enclosure. The main circuit board includes a controller facilitating a physiologic measurement. A display device is connected to the main circuit board that displays information related to the physiologic measurement. A frame is located in the protective enclosure that carries the display device and locates the display device adjacent the front housing such that the display device can be viewed from outside the protective enclosure. The frame includes a strip port formed integrally therewith that is accessible from outside the protective enclosure.

13 Claims, 25 Drawing Sheets

20
30
32
26
28
24
96
92
12
47
51
55
43
46

332
326
334
338
336
324
F

PORTABLE HANDHELD MEDICAL DIAGNOSTIC DEVICES

TECHNICAL FIELD

The present invention relates generally to portable, handheld medical devices, and in particular a portable, handheld medical diagnostic device having a number of improved features.

BACKGROUND

Portable handheld medical diagnostic devices are often employed to measure concentrations of biologically significant components of bodily fluids, such as, for example, glucose concentration in blood. The portable handheld medical diagnostic devices and their accessories may work together to measure the amount of glucose in blood and be used to monitor blood glucose in one's home, healthcare facility or other location, for example, by persons having diabetes or by a healthcare professional.

For people with diabetes, regular testing of blood glucose level can be an important part of diabetes management. Thus, it is desirable to provide medical diagnostic devices that are portable and easy to use. Various medical diagnostic devices have been introduced for testing blood sugar that are portable. However, there continues to be a need for improved portability and ease of use for medical diagnostic devices.

SUMMARY

In one embodiment, a portable handheld medical diagnostic device includes a front housing and a rear housing opposite the front housing. The front housing and the rear housing form a protective enclosure. A main circuit board is located in the protective enclosure. The main circuit board includes a controller facilitating a physiologic measurement. A display device is connected to the main circuit board that displays information related to the physiologic measurement. A frame is located in the protective enclosure that carries the display device and locates the display device adjacent the front housing such that the display device can be viewed from outside the protective enclosure. The frame includes a strip port formed integrally therewith that is accessible from outside the protective enclosure.

In another embodiment, a portable handheld medical diagnostic device includes a front housing and a rear housing connected to the front housing forming a protective enclosure. A main circuit board is located in the protective enclosure. The main circuit board includes a controller facilitating a physiologic measurement. A display device is connected to the main circuit board that displays information related to the physiologic measurement. A strip port is accessible from outside the protective enclosure for inserting a test strip. At least part of the strip port is formed of a material selected for distribution of light to illuminate the at least part of the strip port.

In still yet another embodiment, a method of forming a medical diagnostic device is provided. The method includes providing a frame including a strip port formed with the frame. A display device is mounted on the frame and the frame is positioned adjacent a main circuit board. A protective enclosure is formed with at least a portion of the frame, display and main circuit board located within the protective enclosure by connecting a front housing and a rear housing together. The frame carries the display device adjacent the front housing such that the display device can be viewed from outside the protective enclosure. The strip port is accessible from outside the protective enclosure.

These and other advantages and features of the invention disclosed herein, will be made more apparent from the description, drawings and claims that follow.

BRIEF DESCRIPTION OF THE DRAWINGS

The following detailed description of the embodiments of the present invention can be best understood when read in conjunction with the following drawings, where like structure is indicated with like reference numerals, and in which.

DETAILED DESCRIPTION

The following description of the preferred embodiment is merely exemplary in nature and is in no way intended to limit the invention or its application or uses.

Figure 1:
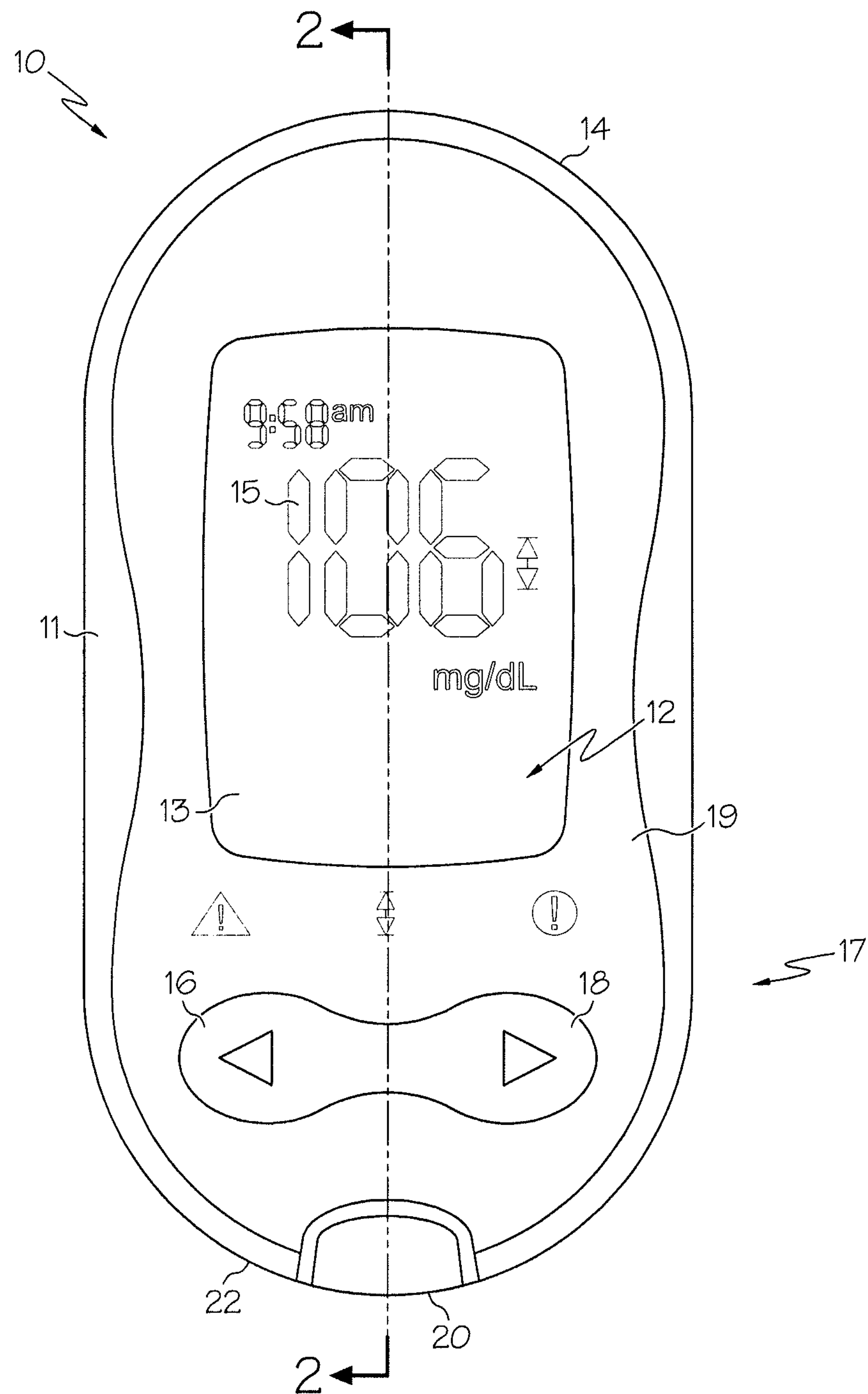
FIG. 1 is a front view of an embodiment of a medical diagnostic device.

Referring to FIG. 1, a portable, handheld medical diagnostic device 10 with a display device 12 behind a transparent, protective lens 13 includes a protective enclosure, generally indicated by symbol 14 that protects electronics therein. The protective enclosure 14 is somewhat oval in shape with an outer frame portion 11 and an inner, hourglass-shaped portion 19 bounded by the frame portion. Any other suitable shapes may be used for the protective enclosure, frame portion 11 and inner portion 19, such as rectangular shapes, circular shapes, etc. The display device 12 may be any suitable display device used in a portable, handheld electronic device, such as, for example, but not limited to LCD display devices, LED display devices, OLED display devices, and other types of display devices which may be heretofore developed. Further, display device 12 may be any other variety of indicators, including, but not limited to a series of lights and/or other types of light devices as opposed to a single integrated display screen. In the illustrated embodiment, the display device 12 includes an electronic paper component such as an electrophoretic display, which may be an information display that forms visible images by rearranging charged pigment particles using an electric field. The display device 12 is used for electronically displaying graphics 15, text, and other elements to a user. In some embodiments, the display device 12 may be a touch-screen user interface that is used with the tip of a finger of the user and/or a stylus or other touching device to select elements from the screen, to draw figures, and to enter text with a character recognition program running on the device 10. In some embodiments, the medical diagnostic device 10 may also include other types of output devices such as for example, sound devices, vibration devices, etc.

The medical diagnostic device 10 further includes a user interface (generally referred to as element 17), which may include buttons 16 and 18. The buttons 16 and 18 are illustrated as right and left arrow buttons, but may be of any other suitable configuration. The buttons 16 and 18 may be used by an operator, for example, to view memory of the medical diagnostic device 10, adjust settings of the device and scroll through test results. The buttons 16 and 18 may be manually actuated, such as by pressing the buttons. In the illustrated embodiment, the buttons 16 and 18 comprise touch sensors (e.g., capacitive touch sensors) that can be actuated by placing a tip of the finger within the button areas. In this embodiment, the buttons 16 and 18 may not move. Instead, the buttons 16 and 18 may be indicated visually to identify where to place the finger. In other embodiments utilizing touch sensors, the buttons 16 and 18 may move, for example, to bring the finger or touching device into close proximity to the touch sensor. In some embodiments, the medical diagnostic device 10 may provide other button or input types such as an OK button and/or joy stick/track ball, which a user may utilize to navigate through a software drive menu provided on the display device 12. Additional buttons may be used as shortcut buttons, for example, to call up a certain program on the medical diagnostic device 10, as a method of scrolling, to select items from a list, or to provide any function that the software designer of the device may assign to the button or set of buttons. Each button size, layout, location, and function may vary for each manufacturer and model of the medical diagnostic device 10.

A test strip port 20 is located at a bottom 22 of the medical diagnostic device 10. The test strip port 20 is sized to receive a test strip for testing a blood sample. In one embodiment, the device 10 is an in vitro diagnostic device that is used to test blood and other body fluids and tissues to obtain information for the diagnosis, prevention and treatment of a disease. The medical diagnostic device 10 may be a self-testing blood glucose meter for people with diabetes. In one embodiment, the medical diagnostic device 10 is a handheld reagent-based blood glucose meter, which measures glucose concentration by observing some aspect of a chemical reaction between a reagent and the glucose in a fluid sample. The reagent may be a chemical compound that is known to react with glucose in a predictable manner, enabling the monitor to determine the concentration of glucose in the sample. For example, the medical diagnostic device 10 may be configured to measure a voltage or a current generated by the reaction between the glucose and the reagent.

A small test strip may be employed to hold the reagent and to host the reaction between the glucose and the reagent mentioned above. Accordingly, in one embodiment of the medical diagnostic device 10 as a blood glucose meter, the test strip port 20 is sized for inserting a test strip into the electronic device 10. The test strip port 20 is used such that the reaction between the glucose and the reagent may be read electronically in order for the medical diagnostic device 10 to determine the concentration of glucose in the sample and display the results to a user. These embodiments enable both health care professionals and patients to perform reliable decentralized testing in hospitals, clinics, offices or patients' homes. In other embodiments, the medical diagnostic device 10 may form part of or include coagulation monitoring systems, professional blood glucose testing and monitoring systems, cardiac marker testing devices, blood gas/electrolyte testing, and urinalysis screening products. In some embodiments, environmental conditions may also be evaluated, for example, using a small AC signal.

Figure 2:
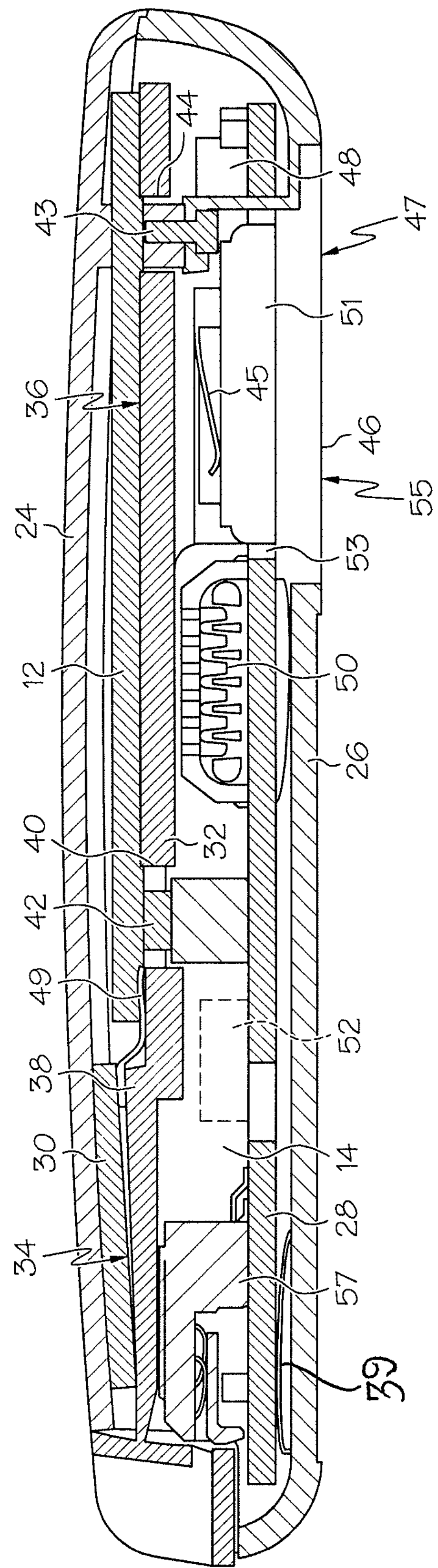
FIG. 2 is a diagrammatic section view of the medical diagnostic device along line 2-2 of FIG. 1.

Referring to FIG. 2, the protective enclosure 14 includes a front housing 24 and rear housing 26. As shown, the front and rear housings 24 and 26 mate to form a protective shell for internal components contained therein, such as for example, the display device 12, a main circuit board 28, and a touch sensor circuit board 30. The front housing 24 and the rear housing 26 may be formed from any of a variety of materials, including but not limited to polymeric materials, metals and metal alloys, combinations of metal and plastic materials, etc. In some embodiments, the front housing 24 and/or rear housing 26 may be formed using an in-mold decoration (IMD) process where a carrier foil that carries indicia is placed in the mold and transfers the indicia onto plastic forming the front and/or rear housing. In another embodiment, the front housing 24 and/or rear housing 26 may be formed by any other suitable process, such as a dual shot molding process. The internal components of the medical diagnostic device 10 may be mounted in the protective enclosure 14 using any number of different mounting techniques. For example, in one embodiment, the internal components of the medical diagnostic device 10 may be mounted via open or closed cell foam inserts provided in the protective enclosure 14, or in another embodiment, they may be mounted via attaching the main circuit board 28 to an interior side of one of the front and rear housings 24 and 26 with a fastener. In another embodiment, the main circuit board may be mounted by a snap fit with an interior side of one of the front and rear housings 24 and 26.

In the embodiment illustrated by FIG. 2, the display device 12 and the touch sensor board 30 are mounted within the protective enclosure 14 by a frame 32. The frame 32 may be formed from any of a variety of materials, including but not limited to polymeric materials, metals and metal alloys, combinations of plastic and metal materials, etc. The frame 32 includes a first board mounting section 34 and a second board mounting section 36. The first board mounting section 34 is shown as being elevated relative to the second board mounting section 36 with a step portion 38 located between the first and second board mounting sections. The first board mounting section 34 may be elevated to place the touch sensor circuit board 30 in close proximity to the front housing 24 and the buttons 16 and 18. Other configurations are possible, however, such as the first and second board mounting sections 34 and 36 being at about the same elevation or the second board mounting section being elevated relative to the first board mounting section. Additionally, there may be more or less than two board mounting portions. The frame 32 includes an opening 40 through which a board-to-board connector 42 extends, such as a 16 or 18 pin connector to connect the display device 12 to the main circuit board 28. The board-to-board connector 42 electrically connects the display device 12 to the main circuit board 28 in a stacked fashion, which situates the major surfaces of both the main circuit board 28 and the display device 12 in somewhat parallel planes within the protective enclosure 14. The frame 32 also includes a fastener opening 44 that receives a fastener 43 for connecting (e.g., threadably connecting) the front housing 24 and the rear housing 26. The fastener 43 can be accessed (e.g., for servicing of the medical diagnostic device 10) through a compartment 47. Other fastener openings and fastener locations may be provided. While the fastener 43 is shown, any suitable connection may be used to connect the front housing and the rear housing such as adhesives, welding, etc. In some embodiments, interlocking features between the front housing 24 and the rear housing 26 may be used to releasably connect the front and rear housings together. In certain embodiments, spring fingers 39 or other biasing mechanism may be used to bias the various components (e.g., touch sensors) toward the front housing 24.

In some embodiments, the main circuit board 28, the frame 32 and the display device 12 may all be different sizes. In other words, a length and width of the main circuit board 28, the frame 32 and the display device 12 may all be different from each other. In some embodiments, two or more of the main circuit board 28, the frame 32 and the display device 12 may have lengths and/or widths that are different from the other(s).

The touch sensor board 30 is connected to the display device 12 using any suitable connector. In the illustrated embodiment, the touch sensor board 30 is connected to the display device 12 using a flex cable connector 49. The flex cable connector 49 may be operatively attached to the touch sensor board 30 and the display device 12 using, for example, a suitable hot bar soldering technique. The connection between the touch sensor board 30 and the display device 12 allows for communication between the touch sensor board 30 and the display device, for example, for control of the display device using information from the user interface 17 (FIG. 1). In some embodiments, the touch sensor board 30 and display device 12 may be part of a single board, thus eliminating the flex cable connector 49.

Referring still to FIG. 2, a power supply 51 is provided within the compartment 47 of the protective enclosure 14 to provide power to the electrical/electronic components of the medical diagnostic device 10, for example, to allow use of the medical diagnostic device without a corded connection to an external power source. In some embodiments and as shown, the power supply 51 is a battery that is received through an opening 53 in the main circuit board 28 such that the battery is located at opposite sides of the main circuit board. Providing such an opening 53 allows the battery to nest with the main circuit board 28, which can reduce the thickness of the medical diagnostic device 10, for example, compared to a device which places the entire battery to only one side of a circuit board. Contacts (only negative contacts 45 are shown by FIG. 2) are provided to connect the power supply 51 to the electrical/electronic components of the medical diagnostic device 10. The power supply 51 is accessed and may be replaceable via a panel 46 provided in the rear housing 26, which provides and prevents access through opening 55 in the rear housing. The panel 46 may include any suitable attachment structure (e.g., a latch, fasteners, etc.) for releasably attaching the panel to the rear housing 26. In some embodiments, the panel 46 may be moveably connected to the rear housing 26 such as by a hinge or a sliding connection. In a rechargeable battery embodiment, the medical diagnostic device 10 may be sealed permanently with the original batteries installed by the manufacturer. In other words, the power supply 51 may not be replaceable. Additional power, such as for recharging the power supply 51, may be provided from a remote source of electricity that is transmitted to the medical diagnostic device 10 through a wire cable or through other methods of electrical transmission. For example, and in one embodiment, the medical diagnostic device 10 is rechargeable via a connected (wired) external device. It is to be appreciated that the medical diagnostic device 10 may provide a universal connection interface, which, in one embodiment, operates is a universal serial bus (USB) interface, and in another embodiment is a Firewire interface, and either of which provides a wired connector which connects to a charger for charging the device 10 via the connected external device.

The main circuit board 28, in one embodiment, provides a wireless connectivity component (generally referred to as element 48) which is used for calibration, configuration, and/or communicate with other devices such as, for example, another meter, an insulin pump, a printer, a router/modem, and/or a PC. In one embodiment, the wireless connectivity component 48 provides infrared communications. In such an embodiment, the medical diagnostic device 10 communicates with a PC running a compatible software package such as, for example, Roche Diagnostic's Accu-Chek Compass diabetes care software via an IrDA-serial port adapter. Such an embodiment permits a user to download data from the medical diagnostic device 10 via the IR based wireless connectivity component 48 and stores results to the PC. In other embodiments, the wireless connectivity component (or module) 48 may be a Bluetooth system, a ZigBee system, a Certified Wireless USB system, a Near Field Communication (NFC) system, an Active RFID system, a Wi-Fi system, and combinations thereof.

A code key interface 50 may also be provided which is used to provide calibration data to a controller (represented by dashed lines 52) via a code key chip and which is used in the measurement of a test strip and in the calculation used to compute the glucose level. A clocking element, such as for example, a 32 kHz crystal, may also be provided on the main circuit board 28 for sampling timing performed by the strip reader and by an integrated digitally controlled oscillator to generate a high-speed clock required for the controller 52 and the other provided peripherals requiring a clock.

A strip reader 57 is located at the test strip port 20. Any suitable strip reader 57 may be used to sample and read a disposable test strip provided to the strip port 20. The strip port 20 guides the test strip into the strip reader 57, which reads the test strip in any suitable manner and provides such input to the controller 52 for analysis.

The front housing 24 and the rear housing 26 provide the protective enclosure 14, which is shaped to accommodate therein the touch sensor board 30, the main circuit board 28, the frame 32 and the power supply 51. However, the shape and dimensions of front and rear housings 24 and 26 of the protective enclosure 14 may vary for each manufacturer and model of the medical diagnostic device 10.

Figure 3:
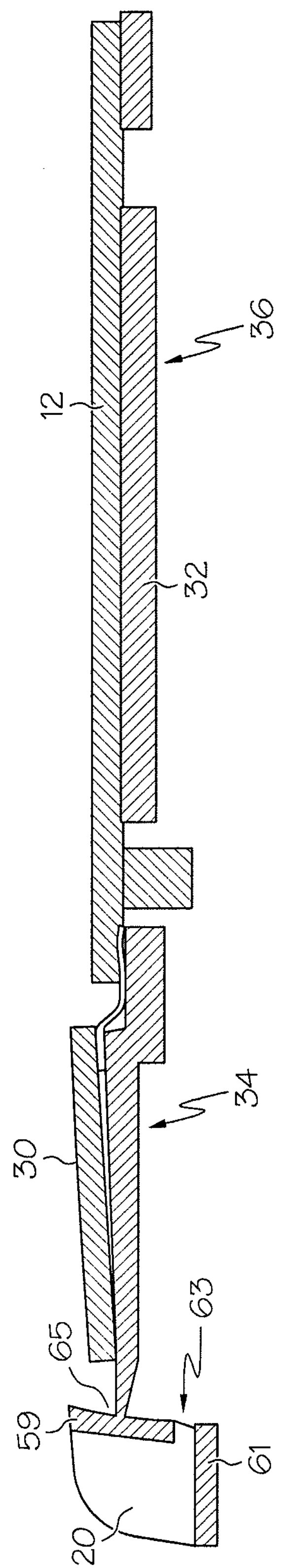
FIG. 3 is a diagrammatic section view of an embodiment of a frame for supporting components of the medical diagnostic device of FIG. 1.

Referring to FIG. 3, the frame 32, display device 12 and touch sensor board 30 are shown in isolation. In one embodiment, the frame 32 is a single piece member (e.g., formed by molding and/or any other suitable method such as machining, extrusion, pressing, etc.) where the test strip port 20 is formed integrally as part of the frame, for example, as opposed to being formed with one or both of the front and rear housings 24 and 26. In one embodiment, the test strip port 20 may be molded of the same material as the frame 32. In another embodiment, the test strip port 20 may be overmolded onto the frame 32, e.g., using the same or a different material as that forming the frame 32. The test strip port 20 includes a vertical portion 59 and a horizontal portion 61. The vertical portion 59 is spaced from the horizontal portion 61 to provide a gap 63 located below the frame 32 through which a test strip can be inserted. The vertical portion 59 is connected integrally to the first board mounting portion 34 at interface 65. In an alternative embodiment, the test strip port 20 may be a separate component and then affixed or connected (e.g., using adhesives, welding, etc.) to the frame 32 or formed with one or both of the front and rear housings 24 and 26. Forming the test strip port 20 with the frame 32 and not the front and rear housings 24 and 26 can facilitate the IMD process used in forming the front and/or rear housings 24 and 26 by reducing the complexity of the mold for forming the front and rear housings. This can improve the reliability of indicia transfer to surfaces of the medical diagnostic device 10 during an IMD process. Additionally, the strip port 20 can be removable from the front and rear housings 24 and 26 when the frame 32 is removed.

Figure 4:
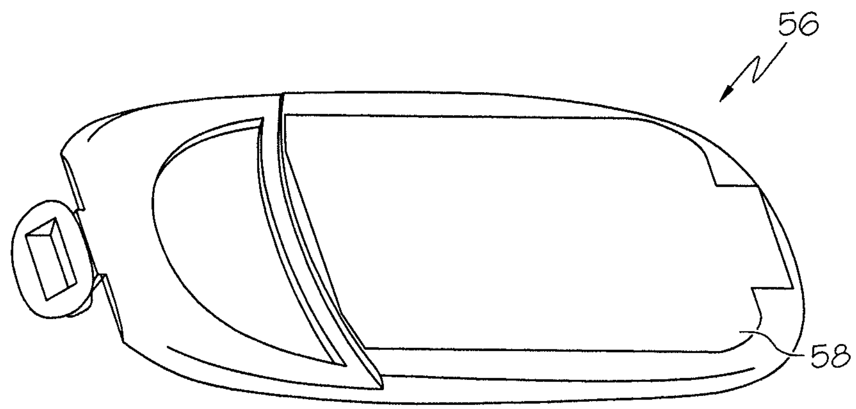
FIG. 4 is a diagrammatic perspective front view of an embodiment of a frame for supporting components of the medical diagnostic device of FIG. 1.
Figure 5:
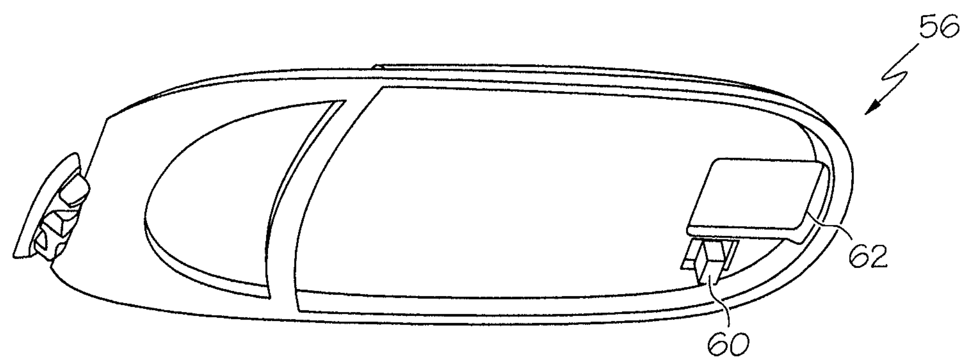
FIG. 5 is a diagrammatic perspective rear view of the frame of FIG. 4.

Referring to FIGS. 4 and 5, one exemplary frame assembly embodiment 56 suitable for use with the medical diagnostic device 10 is illustrated in a simplified form and includes an electronic paper component 58 carried by the frame 56. The electronic paper component 58 may be affixed to the frame 56 using any suitable method such as by adhering the electronic paper component to the frame using, as one example, double-sided tape (e.g., formed of foam). FIG. 5 shows a connector 60 for connecting the electronic paper component 58, for example to the main circuit board 28 and an area 62 for a processor for the electronic paper component.

Figure 6:
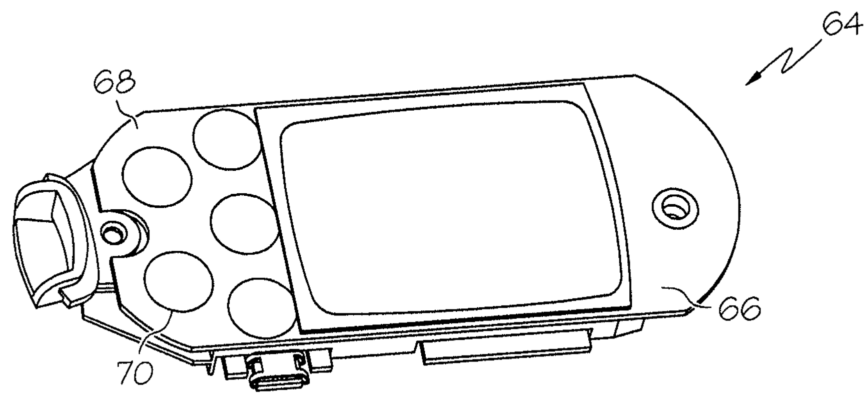
FIG. 6 is a diagrammatic perspective front view of another embodiment of a frame for supporting components of the medical diagnostic device of FIG. 1.
Figure 7:
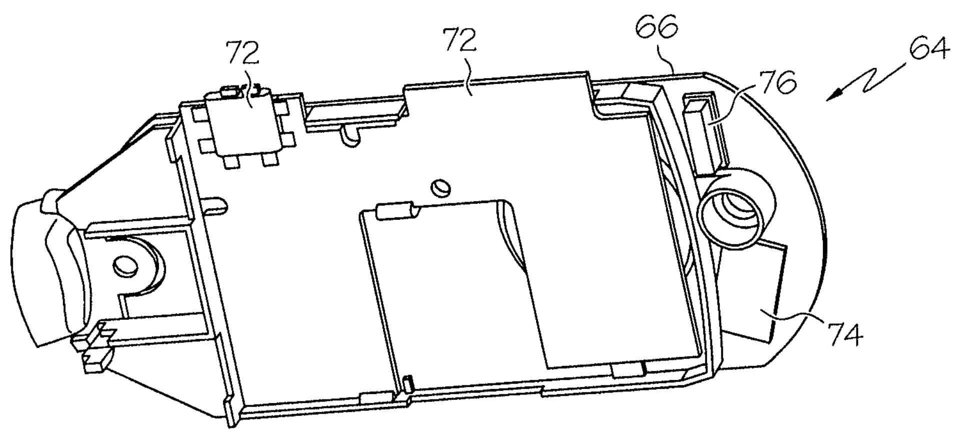
FIG. 7 is a diagrammatic perspective rear view of the frame of FIG. 6.

FIGS. 6 and 7 illustrate another frame assembly embodiment 64 in a simplified form suitable for use with the medical diagnostic device 10. The frame assembly 64 includes an integrated electronic paper component 66 and touch sensor component 68. The integrated electronic paper component 66 and touch sensor component 68 is in contrast to the separate electronic paper component and touch sensor component of FIG. 2. The touch sensor component 68 includes touch sensor pads 70 indicated by circular areas on the touch sensor component, which are aligned with the buttons 16 and 18. Other shapes for the touch sensor pads 70 may be used. Mixed Signal Arrays with On-Chip Controller devices (not shown) may be provided that may provide a low cost single chip programmable component that may include configurable analog and digital blocks and programmable interconnects. Such a device architecture may be used, in some embodiments, to create customized peripheral configurations, for example, to match the requirements of each individual application. Additionally, a CPU, flash program memory, SRAM data memory, and configurable 10 may be included in a range of convenient pinouts.

Referring to FIG. 7, in some exemplary embodiments, a wireless communication board 72 (e.g., a Bluetooth board) is provided on the frame assembly 64. The wireless communication board 72 may include a micro USB, which can be used, for example, to connect the medical diagnostic device 10 with a host computer. An electronic paper display driver 74 may be used to integrate functions needed for functioning of an electronic paper segmented display. Data may be clocked into the device using an interface, such as a SPI serial interface before integrated charge pumps generate the voltages required to drive the display. Once the display has been updated, the driver can be switched into standby or power down mode while still retaining the image on the display. Using advanced packaging techniques, a high level of functionality can fit into a single package, enabling a high density, low footprint design with minimal external components. A connector 76 may be used to connect the electronic paper component 66 to the main circuit board 28.

It should be noted that while touch sensor component 68 is discussed above, a number of other technologies may be used. In some embodiments, the display device 12 itself may be touch sensitive through use of touch screen technology. For example, the display device 12 may include a resistive overlay or a capacitive overlay for detecting the touch of a finger. A resistive touch sensor may employ a flexible membrane positioned over a substrate. Opposing surfaces of the membrane and substrate may be coated with a transparent conductive film. Insulating dot spacers may be interposed between the membrane and the substrate. When the flexible membrane is pressed by a user, the conductive film of the membrane contacts the conductive film of the substrate. This contact causes current to flow between the membrane and substrate. A controller (e.g., controller 52 of FIG. 2) may be used to identify the point of contact by comparing the current flowing from various electrodes or busbars printed on the conductive surfaces. In a capacitive touch sensor, a resistive coating is deposited directly upon a solid, insulating substrate. This substrate may be made of glass, as an example. Electrodes may be positioned at corners of the substrate to establish an electrical field on the coating. A controller (e.g., controller 52 of FIG. 2) connected to these electrodes may be used to monitor the amount of current flowing through each of these electrodes. A user's finger, or a conductive stylus, touching, or coming within close proximity to, the resistive coating causes capacitive coupling between the finger or stylus and the coating. This coupling may cause a small amount of current to flow through the coating and each of the electrodes. Capacitive coupling through the user's body and ground complete the current path back to the controller. The controller may calculate the Cartesian coordinates, i.e., the X and Y coordinates, of the point of touching from the amount of current flowing through each of these electrodes. In some embodiments, capacitive touch sensing is preferred. It is also contemplated that acoustic wave technology or infrared technology may be used. Shutter technology may be used to provide various indications to the user, for example, by selectively illuminating buttons to prompt a user.

Figure 8:
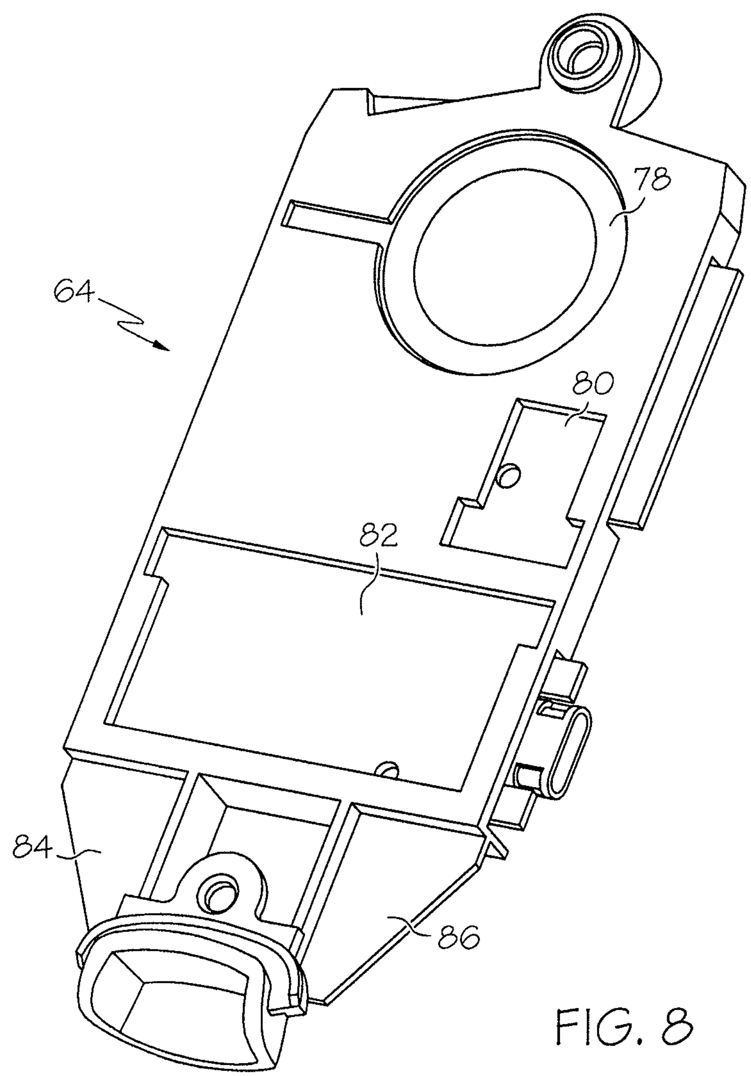
FIG. 8 is a diagrammatic perspective top view of the frame of FIG. 6 with components removed.

Referring to FIG. 8, the frame assembly 64 is shown with the electronic paper component 66 and touch sensor component 68 removed. An audio component 78, such as a buzzer, is carried by the frame assembly 64, beneath the electronic paper component 66. Areas 80 and 82, which are formed by openings through the frame assembly, are provided for the wireless communication board 72 components. Insets 84 and 86 are provided to allow mounting of the controller devices and other components for the touch sensor component 68.

Figure 9:
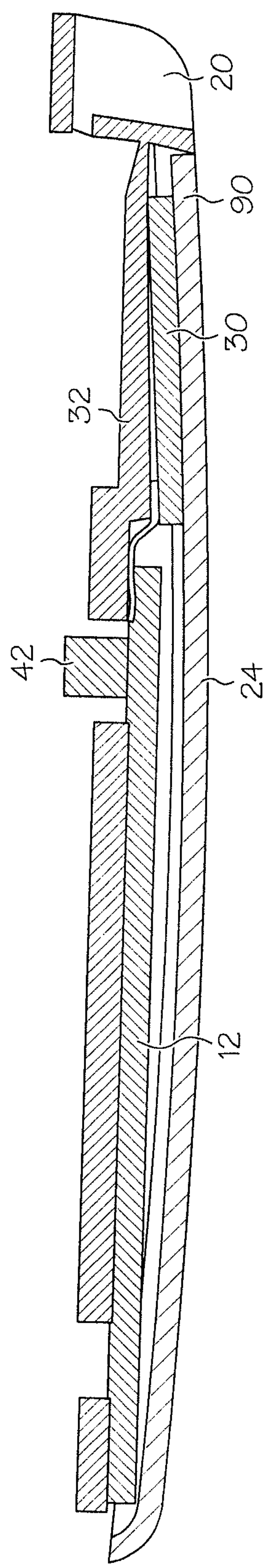
FIGS. 9-11 illustrate an embodiment of a process for assembling the medical diagnostic device of FIG. 1.
Figure 10:
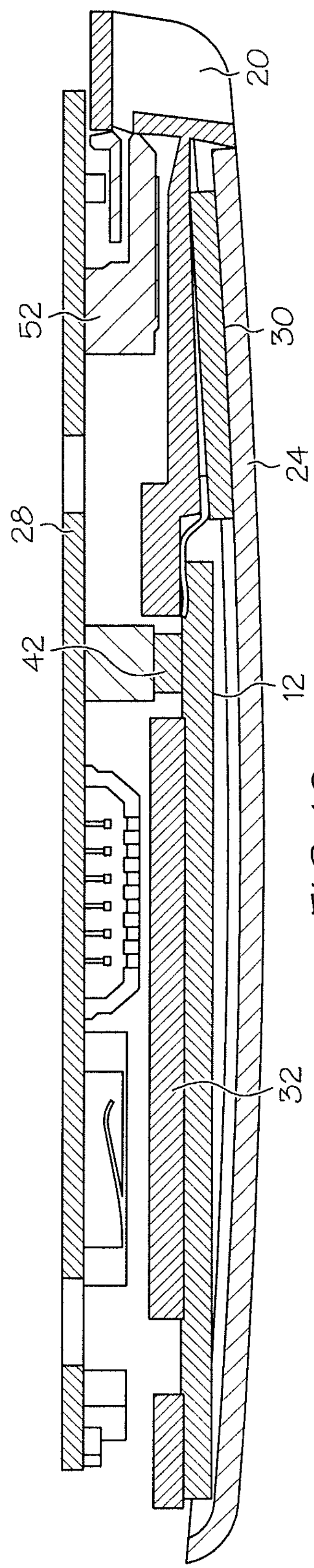
Figure 11:
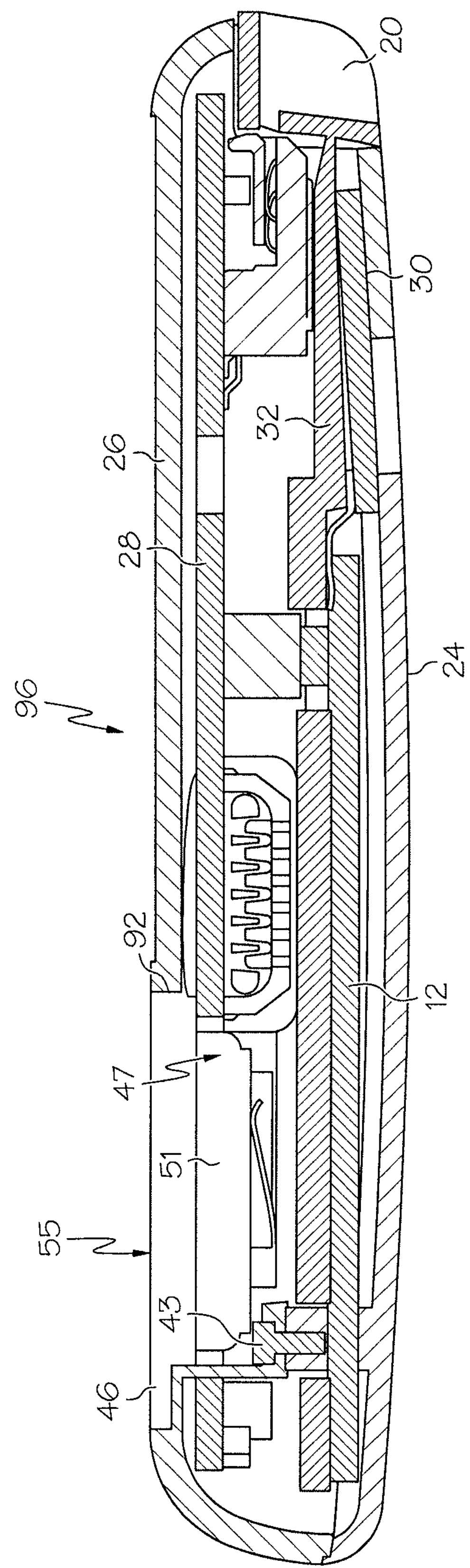

Referring now to FIGS. 9-11, a process is illustrated for assembling the medical diagnostic device 10. Referring to FIG. 9, in one embodiment of the exemplary process of assembly, the frame 32 with the display device 12 and touch sensor board 30 affixed thereto is placed onto the front housing 24 to align the display device 12 with the protective lens 13 (FIG. 1) of the front housing 24 and the sensor pads (e.g., see the sensor pads 70 of FIG. 6) with the buttons 16 and 18 (see FIG. 1). The test strip port 20 is aligned with a bottom edge 90 of the front housing 24. Referring to FIG. 10, the main circuit board 28 is connected to the display device 12 using the connector 42 and the test strip reader 57 is aligned with the test strip port 20. Referring to FIG. 11, the rear housing 26 is then connected to the front housing the fastener 43, which can be secured through the compartment 47. The power supply 51 may be inserted into the compartment 47 through opening 92 in the rear housing 26. The panel 46 may be used to close the opening 55 and secure the power supply 51 within the compartment 47. Any labels may be affixed to the rear housing (represented by arrow 96).

Figure 12:
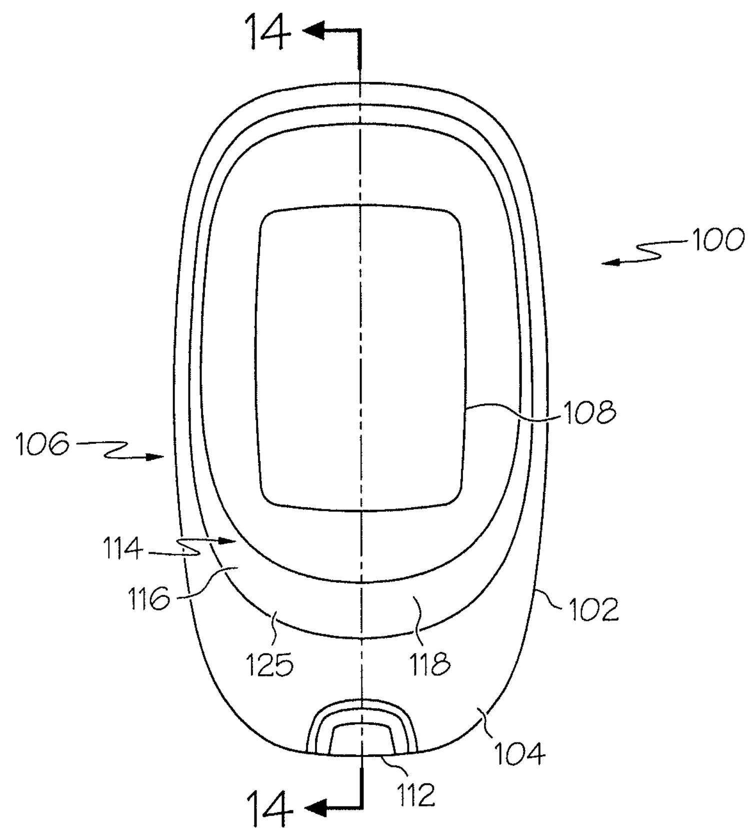
FIG. 12 is a front view of another embodiment of a medical diagnostic device.
Figure 13:
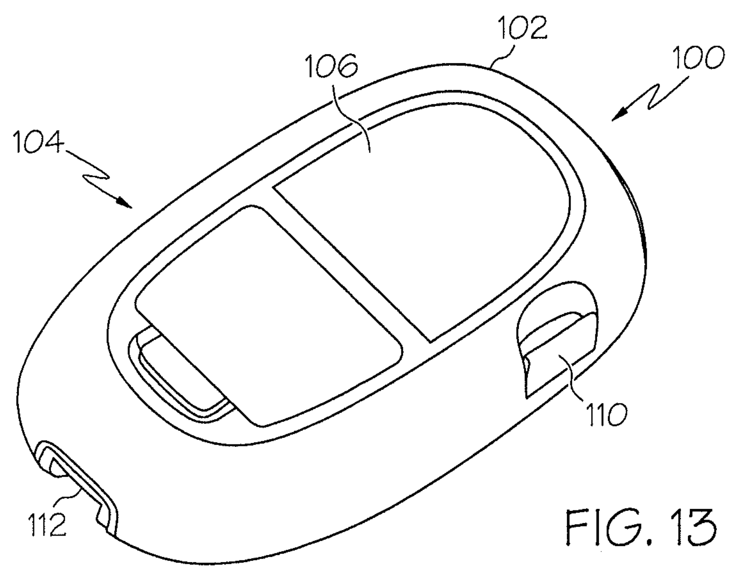
FIG. 13 is a perspective rear view of the medical diagnostic device of FIG. 12.

Referring to FIGS. 12 and 13, in another embodiment, a medical diagnostic device 100 has many of the features described above with regard to medical diagnostic device 10 including a protective enclosure 102 formed by a front housing 104 and a rear housing 106, a display device 108 visible through the front housing, a key card interface 110 and a strip port 112. In this embodiment, the display device 108 may be an LCD display device, however, the display device may be LED display devices, OLED display devices, display devices utilizing e-paper and other types of display devices which may be heretofore developed. The display device 108 is used for electronically displaying graphics, text, and other elements to a user. In some embodiments, the display device 108 may also be a touch-screen user interface that is used with the tip of a finger of the user and/or a stylus or other touching device to select elements from the screen, to draw figures, and to enter text with a character recognition program running on the device 100. In some embodiments, the medical diagnostic device 100 may also include other types of output devices such as for example, sound devices, vibration devices, etc.

As above, the medical diagnostic device 100 is provided with a user interface 114 to operate and interact with the features of the medical diagnostic device 100. The user interface 114 of this embodiment includes buttons 116 and 118 (e.g., formed by a single deflectable component 146), for controlling features such as power, program navigation, selection, and data entry. As shown, the user interface 114 is provided on the front housing 104 of the medical diagnostic device 100 adjacent the display device 108. In one embodiment, the medical diagnostic device 100 provides a right button 118, a left button 116, and/or joy stick/track ball (not shown), which a user uses to navigate through a software drive menu provided on the display device 108. In other embodiments, additional buttons may be used as shortcut buttons to call up a certain program on the medical diagnostic device 100, may comprise a method of scrolling, may be used to select items from a list, or may have any function that the software designer of the device may assign to the button or set of buttons. Each button size, layout, location, and function may vary for each manufacturer and model of the device 100.

In contrast to the touch sensor buttons 16 and 18 described above with reference to diagnostic medical device 10, the buttons 116 and 118 are actuated by pressing the deflectable component 146 inwardly using manually applied pressure. The buttons 116 and 118 are outlined by a groove 125 formed in the front housing 104, which allows the deflectable component 146 to be actuated relative to the front housing 104.

Figure 14:
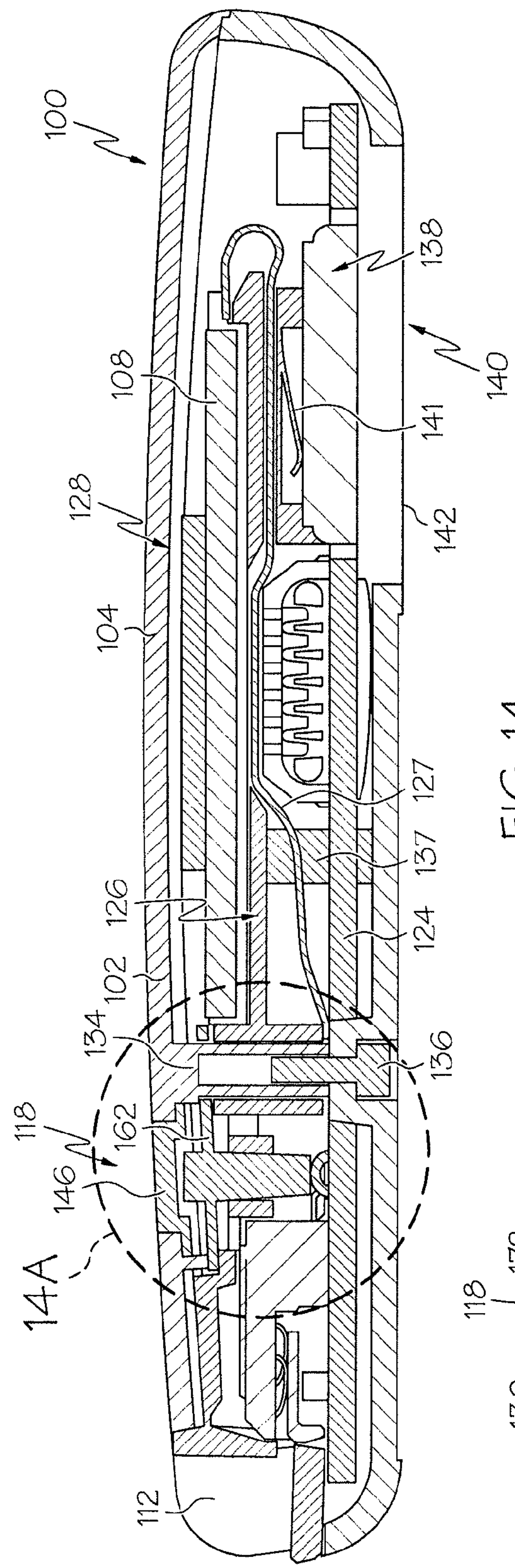
FIG. 14 is a diagrammatic section view of the medical diagnostic device along lines 14-14 of FIG. 12.

Referring to FIG. 14, the protective enclosure 102 includes the front housing 104 and the rear housing 106. The front and rear housings 104 and 106 mate to form a protective shell for internal components contained therein, such as for example, the display device 108 and a main circuit board 124 connected to the display device by any suitable connector, such as flex cable 127. Unlike the medical diagnostic device 10, the medical diagnostic device 100 may not include a touch sensor circuit board as the buttons 116 and 118 may be manually actuated. In alternative embodiments, the medical diagnostic device 100 may include a touch sensor circuit board and touch sensor buttons. The internal components of the medical diagnostic device 100 may be mounted in the protective enclosure 102 using any number of different mounting techniques. For example, in one embodiment, the internal components of the medical diagnostic device 100 may be mounted via open or closed cell foam inserts provided in the protective enclosure 102, or in another embodiment, they may be mounted via attaching the main circuit board 124 to an interior side of one of the front and rear housings 104 and 106 with a fastener. In another embodiment, the main circuit board 124 may be mounted by a snap fit with an interior side of one of the front and rear housings 104 and 106.

In the embodiment illustrated by FIG. 14, the display device 108 is mounted within the protective enclosure 102 by a frame 126. The frame 126 may be formed from any of a variety of materials, including but not limited to polymeric materials, metals and metal alloys, combinations of plastic and metal materials, etc. The frame 126 includes a board mounting section 128 and a user interface mounting section 130. The frame 126 includes an opening 132 through which a fastening boss 134 extends. The fastening boss 134 receives fastener 136 to connect the front housing 104 to the rear housing 106 and also may be used to align the internal components of the medical diagnostic device 100. The fastener 136 may be accessed from the rear housing 106. While the fastener 136 is shown, any suitable connection may be used to connect the front housing and the rear housing such as adhesives, welding, etc. A guide pin 137 may extend downwardly from the frame 126 toward the rear housing 106. The guide pin 137 may be received within an alignment opening 139 (FIG. 16) extending through the main circuit board 124. The guide pin 137 may be used to align the internal components and also to maintain spacing of the frame 126 from the rear housing 106.

A power supply 138 is provided within the protective enclosure 102 to provide power to the electrical/electronic components of the medical diagnostic device 100. The power supply 138 may be, for example, a battery that is received through an opening 140 in the main circuit board 124. Contacts (only negative contacts 141 are shown by FIG. 14) are provided to connect the power supply 138 to the electrical/electronic components of the medical diagnostic device 100. The power supply 138 is accessed and may be replaceable via a panel 142 provided in the rear housing 106 (see FIG. 13). In a rechargeable battery embodiment, the medical diagnostic device 100 may be sealed permanently with the original batteries installed by the manufacturer. As indicated above, additional power may be provided to the power supply 138 using any suitable methods.

The frame 126 is used to mount a button actuation assembly (indicated generally as element 144) at the interface mounting section 130. The buttons 116 and 118 (only button 116 can be seen in FIG. 14) are formed by the deflectable component 146 (e.g., formed of any suitable material such as rubber, plastic, metal, etc.) movably mounted to the front housing 104 by any suitable method such that the deflectable component can be deflected by manually applied pressure. In some embodiments, the deflectable component 146 may be biased outwardly toward an undeflected (i.e., unactuated) position using springs, elastic material, etc. The deflectable component 146 includes a lip 148 that engages an inner surface 150 of the front housing 104 with the inner surface 150 overhanging the lip. The lip 148 prevents removal of the deflectable component 146 from the front housing 104 and may be used to position the deflectable component in its undeflected position.

The button actuation assembly 144 includes a post 152 that extends vertically within the protective enclosure 102 between a contact dome 154 and the deflectable component 146. The post 152 may be formed of any suitable material such as rubber, plastic, etc. In one embodiment, the deflectable component 146 may be formed of a relatively hard material, such as a hard plastic material while the post 152 may be formed of a different, relatively soft material. The post 152 may be used to bias the deflectable component 146 toward its undeflected position. The post 152 is slidably received within a guide slot 156 that is formed by a post guide 158 provided by the frame 126. The post guide 160, in some embodiments, is formed as part of the frame 126 and extends vertically along a length of the post 152. Alternatively, the post guide 160 may be formed as a separate component and be formed using a low friction material to facilitate sliding movement of the post 152 within the guide slot 156.

A membrane 162 is captured between the frame 126 and the front housing 104. The membrane 162 may be formed of a flexible, elastic material such as rubber or plastic. In some embodiments, the membrane 162 may be formed with the post 152, extending integrally outwardly from the post. In other embodiments, the membrane 162 may be formed separately from the post 152 and attached thereto by any suitable method, such as by welding, adhesives, etc. As indicated above, the groove 125 is provided between the deflectable component 146 and the front housing 104 to allow the deflectable component to deflect relative to the front housing. The groove 125, however, may provide a potential leak path that might allow fluids and other particles to enter the protective enclosure 102. Such fluids and contaminants may damage the main circuit board 124 should they come into contact therewith. Thus, the membrane 162 serves as a barrier between the deflectable component 146 and the main circuit board 124.

Figure 15:
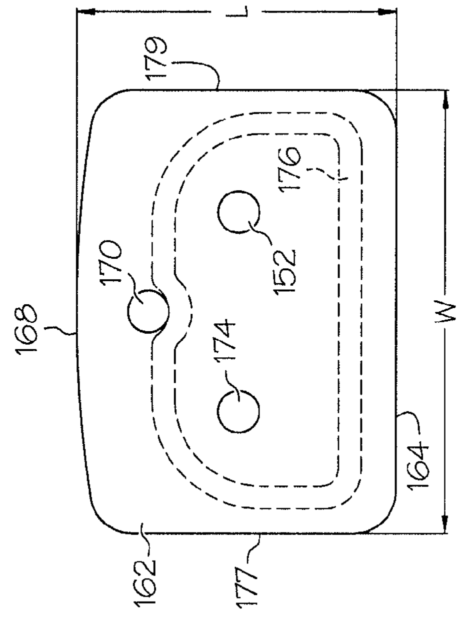
FIG. 15 is a diagrammatic top view of an embodiment of a button actuation assembly for use in the medical diagnostic device of FIG. 12.
Figure 14A:
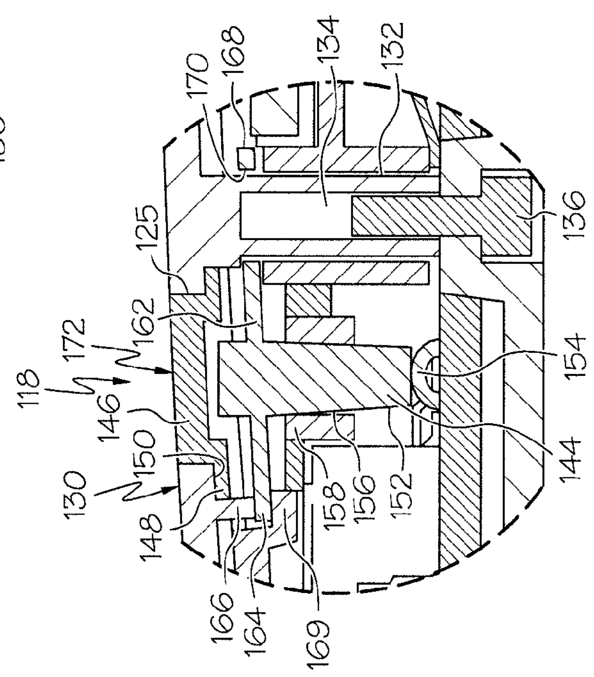

The membrane 162 may be located within the protective enclosure 102 using any suitable connection. In the illustrated embodiment, the membrane 162 includes a first end 164 that is captured or pinched between a projection 166 extending inwardly from the front housing 104 and a ledge 169 of the frame 126. The membrane 162 includes an opposite end 168 including an opening 170 extending therethrough that is sized to receive the fastening boss 134. In some embodiments, the membrane 162 has a length L measured between the ends that is longer than an opening 172 that receives the buttons 116 and 118 and a width W measured between sides 177 and 179 (FIG. 15) that is wider than a width of the opening 172. FIG. 15 shows one illustrative embodiment where the post 152 associated with the button 118 and a second post 174 associated with the button 116 are both connected to the same membrane 162, which extends beyond the opening 172 that receives the buttons. As represented by the dotted lines, the projection 166 can engage the membrane 162 at area 176 and the fastening boss 134 can pass through the opening 170. In some embodiments, the opening 170 may be sized slightly smaller than the cross-sectional dimensions of the fastening boss 134 to frictionally engage the fastening pin when inserted through the opening 170.

Figure 17:
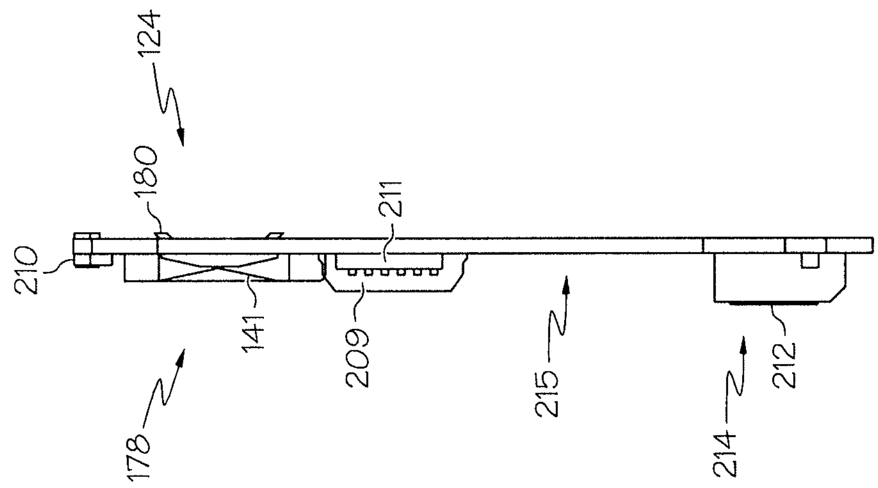
FIG. 17 is a diagrammatic side view of the main circuit board of FIG. 16.
Figure 16:
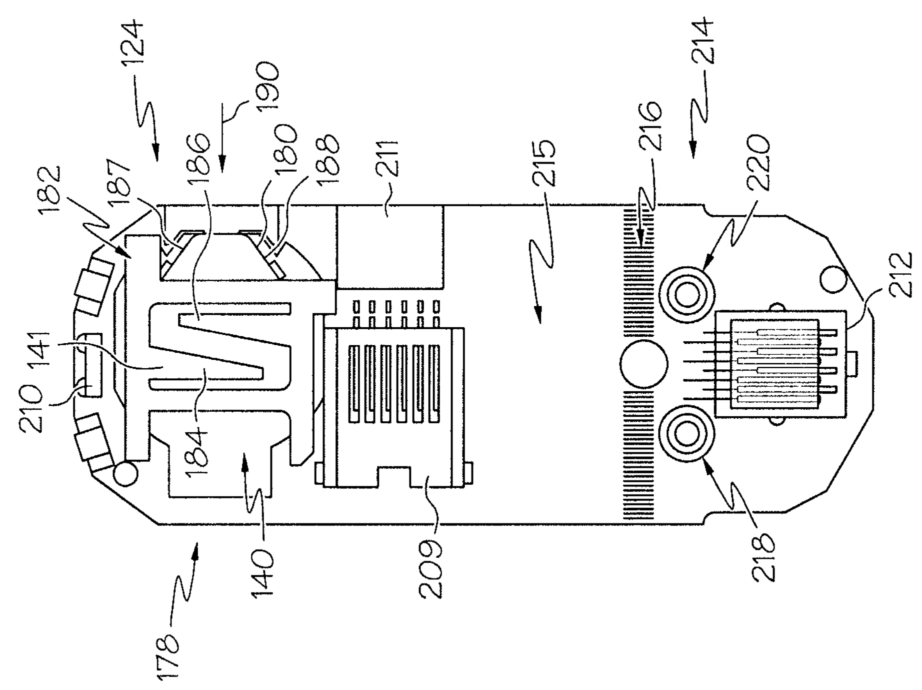
FIG. 16 is a diagrammatic top view of an embodiment of a main circuit board for use in the medical diagnostic device of FIG. 12.

FIGS. 16 and 17 illustrate an exemplary embodiment of the main circuit board 124. The main circuit board 124 includes an upper region 178 including the opening 140 that is sized to receive the power supply 138, negative contacts 141 and positive contacts 180. Negative contacts 141 include an outer frame member 182 that connects to the main circuit board 124. The contact arms 184 and 186 span at least part of the opening 140 so that the power supply 138 can seat against the contact arms of the negative contacts (see also FIG. 14). As shown most clearly by FIG. 17, the frame member 182 extends outwardly from the main circuit board 124 forming a pocket that receives the power supply 138. The positive contacts 180 are also mounted to the main circuit board 124 and include a pair of spring arms 187 and 188 located to a side of the opening 140. In some embodiments, the spring arms 187 and 188 provide a sufficient bias force to move the power supply 138 in the direction of arrow 190 (e.g., with the power supply in the opening 140) to an opposite side of the opening 140 once the power supply is inserted through the opening 140.

Figure 18:
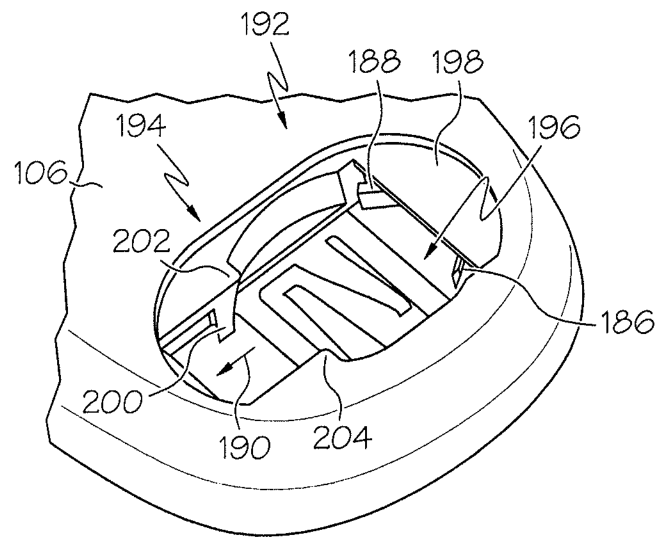
FIG. 18 is a diagrammatic detail view of an embodiment of a power supply compartment for use with the diagnostic medical device of FIG. 12.
Figure 19:
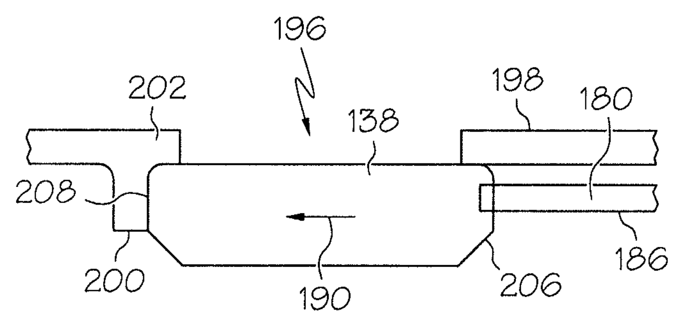
FIG. 19 is a diagrammatic side view of an embodiment of a power supply insertion procedure of the power supply compartment of FIG. 18.

Referring briefly to FIG. 18, compartment 192 has a locking feature (generally designated as element 194) that inhibits unintended removal of the power supply 138 from the compartment 192, even when the panel 142 is removed. The rear housing 106 includes an insertion aperture 196 that is sized and arranged to guide the power supply 138 against the spring arms 187 and 188 thereby deflecting the spring arms. To insert the power supply 138, an edge of the power supply is inserted through the insertion aperture 196 and placed beneath a ledge 198 to locate the power supply in an insertion position, which deflects the spring arms 187 and 188. The spring arms 187 and 188, when deflected, provide a sufficient spring force to push the power supply 138 in the direction of the arrow 190, against a stop 200 and beneath overhanging portions 202 and 204 to a lock position without touching the power supply. FIG. 19 illustrates the power supply 138 in the lock position where a first side 206 of the power supply in contact with the positive contacts 180 is beneath the ledge 198 and an opposite side 208 of the power supply is against the stop 200 and beneath the overhanging portions 202 and 204. Thus, to remove the power supply 138 from the compartment 192, a user applies a force to the power supply opposite arrow 190 sufficient for deflecting the spring arms 187 and 188 to place the power supply in the insertion position. Then, side 208 of the power supply 138 can be lifted through the insertion aperture 196 and the power supply can be removed from the compartment 192.

Referring back to FIGS. 16 and 17, as above, a wireless connectivity component (generally referred to as element 210) may be provided at the upper region 178 which may be used for calibration, configuration, and/or communicate with other devices such as, for example, another meter, an insulin pump, a printer, a router/modem, and/or a PC. In one embodiment, the wireless connectivity component 210 provides infrared communications. A code key interface 209 may also be provided which is used to provide calibration data to a controller via a code key chip and which is used in the measurement of a test strip and in the calculation used to compute the glucose level. A sound device 211, such as a beeper (e.g., a piezo beeper) may be mounted on the main circuit board 124. Alternatively, the sound device may be mounted on the display device 108. A strip reader 212 is located at a bottom region 214 of the main circuit board 124 at the test strip port 112. In one embodiment, the strip reader 212 is configured to sample and read a disposable test strip provided to the strip port 112. The strip port 112 is used to connect the test strip electrically to the strip reader 212, which reads the test strip electronically in any suitable manner and provides such input to a controller for analysis. Area 215, in some embodiments, may be reserved for the controller or meter engine. Area 216 may be reserved for the flex cable 127 (e.g., hot bar), an e-link (X pin connector), or any other suitable connector, for example, that connects the display device 108 to the main circuit board 124. Regions 218 and 220 may be landing areas for the metal domes 154. In an alternative embodiment, the regions 218 and 220 may be replaced with touch sensors, as described above.

Figure 20:
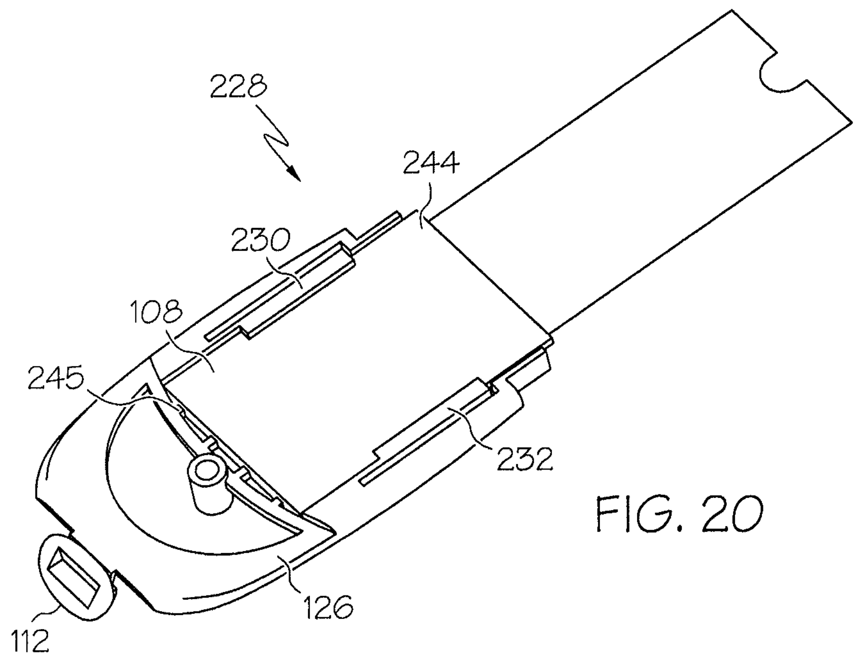
FIG. 20 is a diagrammatic perspective top view of an embodiment of a frame for use in the medical diagnostic device of FIG. 12.
Figure 21:
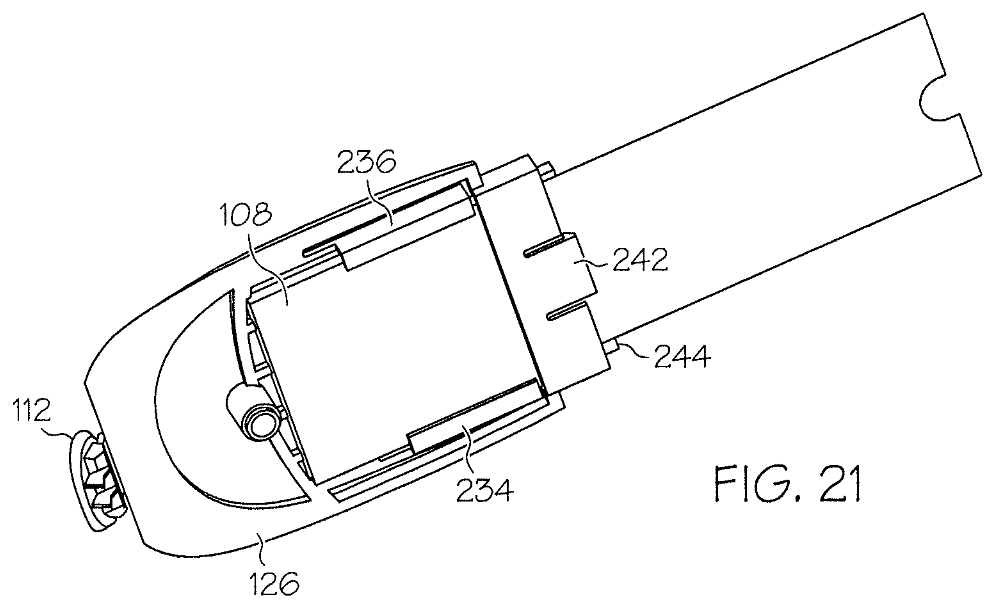
FIG. 21 is a diagrammatic perspective rear view of the frame of FIG. 20.
Figure 22:
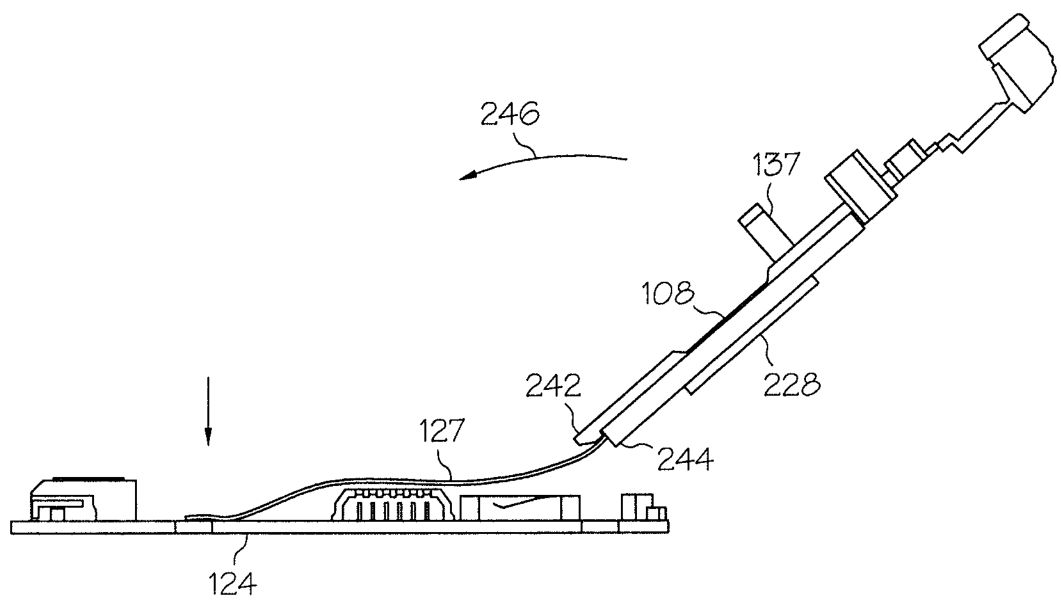
FIGS. 22-26 illustrate an embodiment of a process for assembling the medical diagnostic device of FIG. 12.

Referring to FIGS. 20 and 21, an exemplary frame 126 and the display device 108 are shown in isolation. In one embodiment, the frame 126 is a single piece member (e.g., formed by molding) where the test strip port 112 is formed integrally as part of the frame as opposed to being formed with one or both of the front and rear housings 104 and 106. In one embodiment, the test strip port 112 may be overmolded onto the frame 126. In an alternative embodiment, the test strip port 112 may be a separate component or formed with one or both of the front and rear housings 104 and 106. Forming the test strip port 112 with the frame 126 and not the front and rear housings 104 and 106 can facilitate the IMD process used in forming the front and/or rear housings by reducing the complexity of the mold for forming the front and rear housings. This can improve the reliability of indicia transfer to surfaces of the medical diagnostic device 100 during an IMD process. In some embodiments, a double shot molding process may be used in forming the front housing 104 and/or the rear housing 106. Additionally, the strip port 112 can be removable from the front and rear housings 104 and 106 when the frame 126 is removed.

The frame 126 includes a bracket assembly, generally referred to as element 228, that mounts the display device 108 to the frame. The bracket assembly 228 includes front bracket members 230 and 232 and rear bracket members 234 and 236. The front and rear bracket members 230, 234 and 232, 236 cooperate to hold the display device 108 in place within the compartment 192, preventing lifting movement off of the frame by overhanging at least a portion of the display device and preventing side-to side movement of the display device by engaging sides 238 and 240 of the display device. A connector 242 (e.g., snap, hook, etc.) is located at a rear of the frame 126 and is used to releasably engage a lower edge 244 of the display device 108, preventing top-to-bottom sliding movement of the display device 108 from the bracket assembly 228. The connector 238 holds the display device 108 against stop members 245, which engage an upper edge 244 of the display device.

Figure 23:
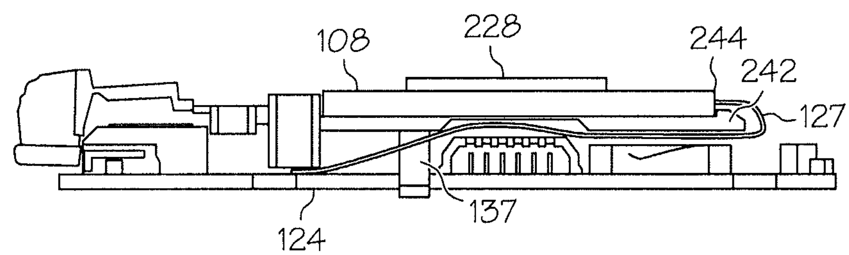

Referring now to FIGS. 22-25, a process is illustrated for assembling the medical diagnostic device 100. At FIG. 22, the display device 108 is inserted into the bracket assembly 228 until the lower edge 244 of the display device clears the connector 242 such that the connector 242 hooks or engages the lower edge of the display device. The flex cable 127 is connected to the main circuit board 124 at area 216. With the display device 108 carried by the frame 126 and the flex cable 127 connected to the main circuit board 124, the frame is rotated in the direction of arrow 246 to insert the guide pin 137 into the alignment opening 139 (FIG. 16) extending through the main circuit board. FIG. 23 illustrates the frame 126 with the display device 108 connected to the main circuit board 124. As can be seen, the flex cable 127 runs from the main circuit board 124, along a length of the assembly between the frame 126 and the main circuit board 124 and over an edge of the frame to the display device 108.

Figure 24:
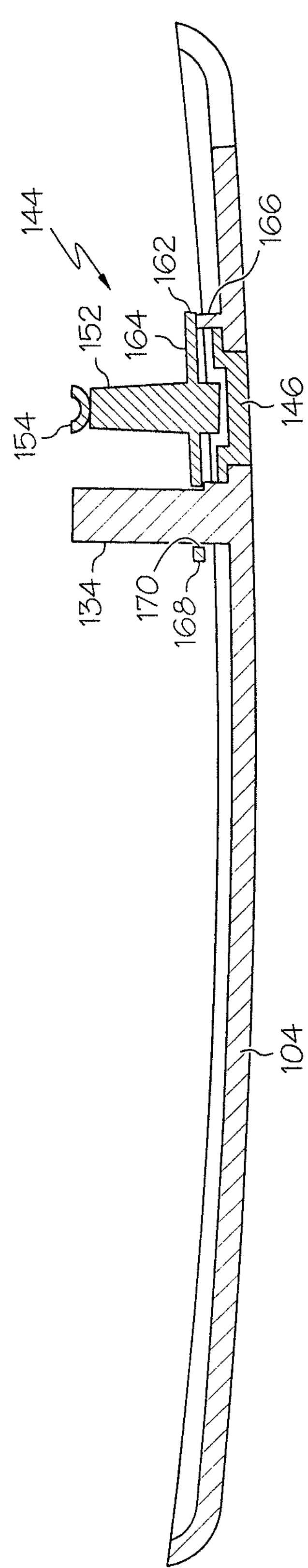

Referring to FIG. 24, the deflectable component 146 which forms the buttons 116 and 118 is seated within the opening in the front housing 104. The button actuation assembly 144 including the post 152, dome 154 and membrane 162 are assembled onto the deflectable component 146. The fastening boss 134 is inserted through the opening 170 in the membrane 162 at the end 168 and the opposite end 164 is located adjacent the projection 166. The contact dome 154 is placed on the post 152.

Figure 25:
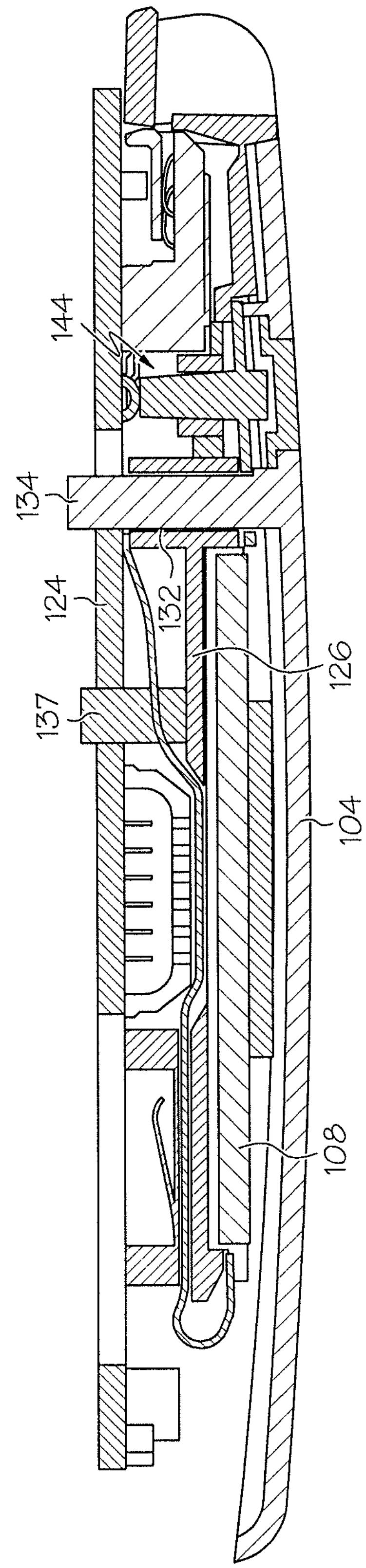
Figure 26:
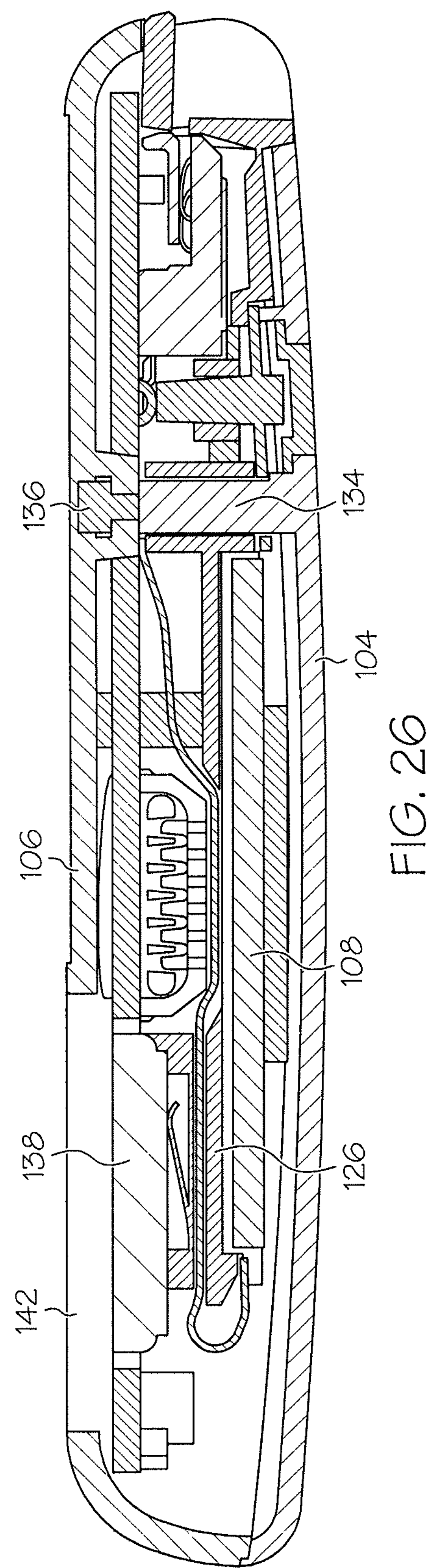

Referring to FIG. 25, the frame 126, display device 108 and main circuit board 124 assembly (FIG. 23) are placed or dropped onto the front housing 104 with button actuation assembly 144 (FIG. 24) such that the fastening boss 134 is inserted through the opening 132 in the frame 126. The end 164 of the membrane 162 is pinched between the projection 166 and the ledge 169 of the frame 126. Referring to FIG. 26, the rear housing 106 is placed or dropped onto the front housing 104 and frame 126 assembly and the fastener 136 is used to releasably secure the front and rear housings together by engaging the fastener 136 with the fastening boss 134 (e.g., through a threaded connection). The power supply 138 may then be installed as described above with reference to FIGS. 18 and 19 and the panel 142 secured to the rear housing 106.

Figure 27:
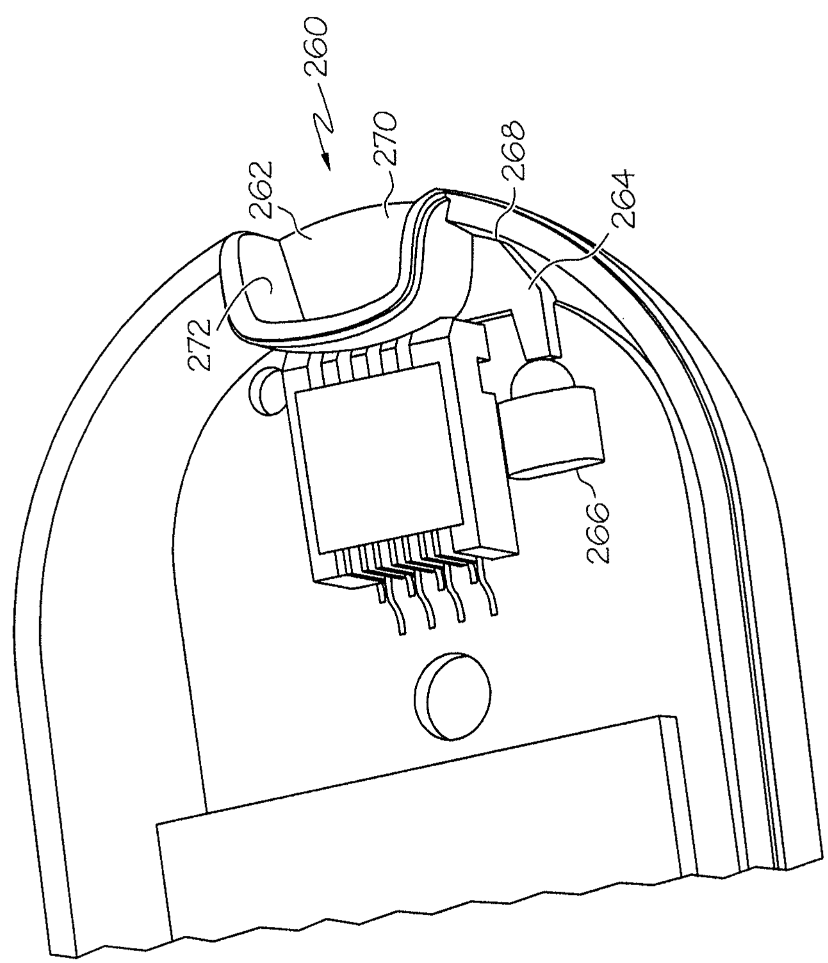
FIG. 27 is a diagrammatic detail view of an embodiment of an illuminated strip port.

Referring to FIG. 27, the above described diagnostic medical devices 10 and 100, in some embodiments, may include an illuminated strip port assembly 260. The illuminated strip port assembly 260 includes a strip port 262, a light pipe 264 and a light source 266 (e.g., an LED). A light pipe 264 is a tube or pipe for transport of light from one location to another location while minimizing the loss of light. The light pipe 264 may be formed of any suitable material, such as glass, plastic or a pipe with a highly reflective lining. The light pipe 264 transmits light from the light source 266 to the strip port 262 (or a portion thereof). The strip port 262 may be formed of a material selected for distribution of light over its length, either for equidistribution along the entire length or for controlled light leakage. The strip port 262 may be formed of any suitable material such as glass, plastic, etc. In the illustrated embodiment, the light pipe 264 may be formed of molded plastic with one or more prismatic turns 268 so that light reflects off the turns and does not travel straight into the strip port 262. In one embodiment, only a bottom shelf 270 of the strip port 262 may illuminate (e.g., the bottom shelf may be formed separately and/or of a different material than the rest of the strip port such as vertical wall 272). In another embodiment, the entire strip port 262 may illuminate. In some embodiments, the LED may be capable of providing a number of different colors for illuminating the strip port 262 using different color lighting. The different colors may provide different indications to a user. In some embodiments, the lighting is selected to illuminate the strip port 262 to allow a user to use the medical diagnostic devices 10 and 100 in the dark.

Figure 28:
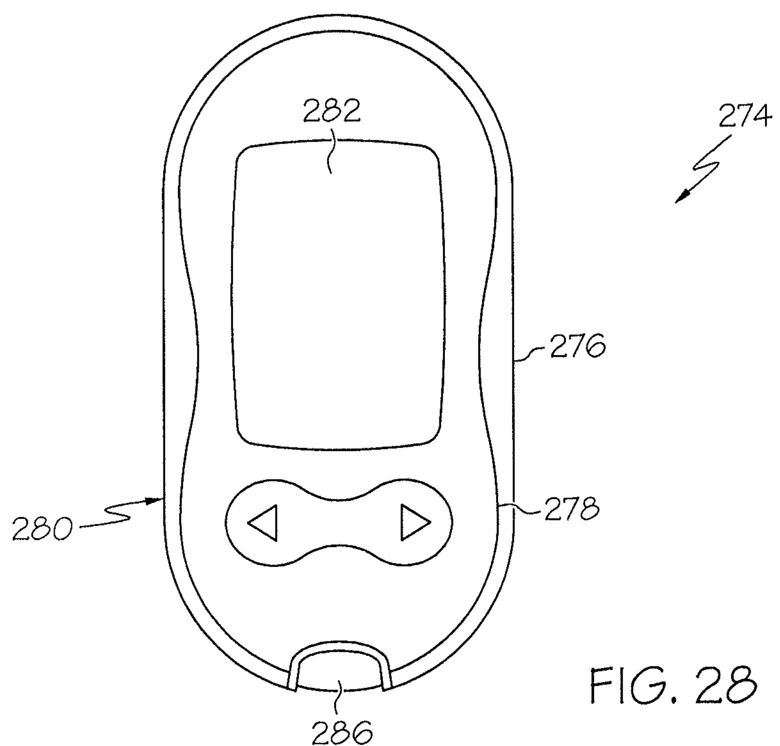
FIG. 28 is a front view of another embodiment of a medical diagnostic device.
Figure 29:
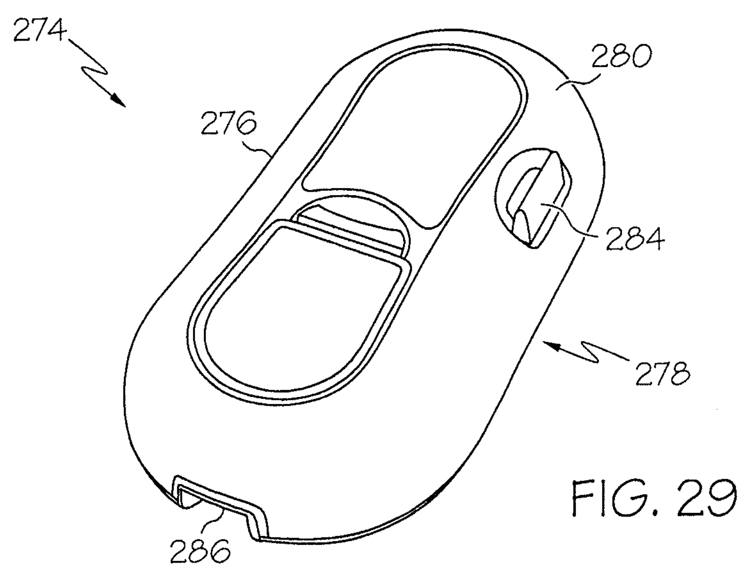
FIG. 29 is a perspective rear view of the medical diagnostic device of FIG. 28.

Referring to FIGS. 28 and 29, in another embodiment, a medical diagnostic device 274 has many of the features described above with regard to medical diagnostic devices 10 and 100 including a protective enclosure 276 formed by a front housing 278 and a rear housing 280, a display device 282 visible through the front housing, a key card interface 284 and a strip port 286. In this embodiment, the display device 282 may be an LCD display device, however, the display device may be LED display devices, OLED display devices, display devices utilizing e-paper and other types of display devices which may be heretofore developed.

Figure 31:
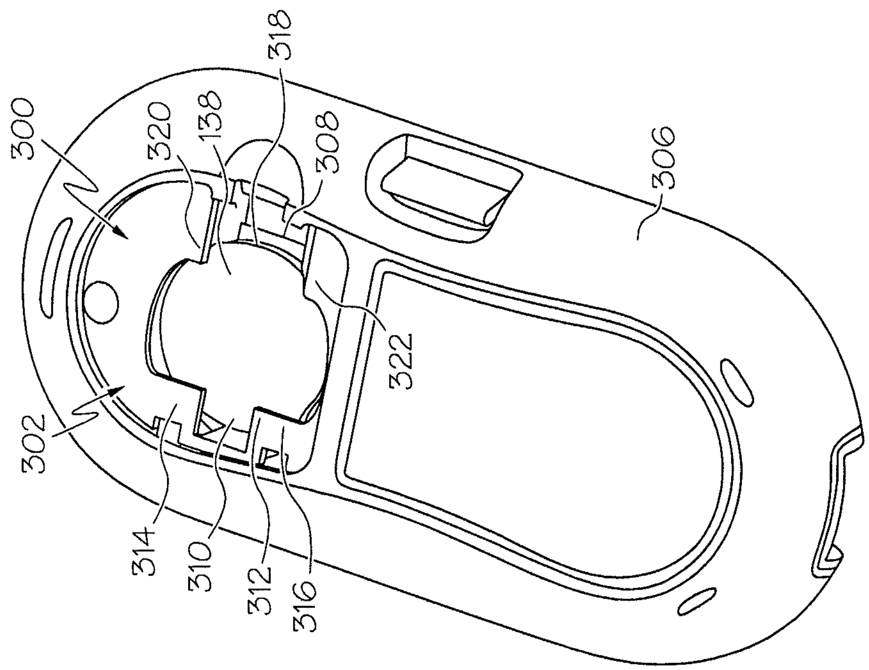
FIG. 31 is a perspective rear view of the diagnostic medical device of FIG. 30 with a compartment panel removed.
Figure 30:
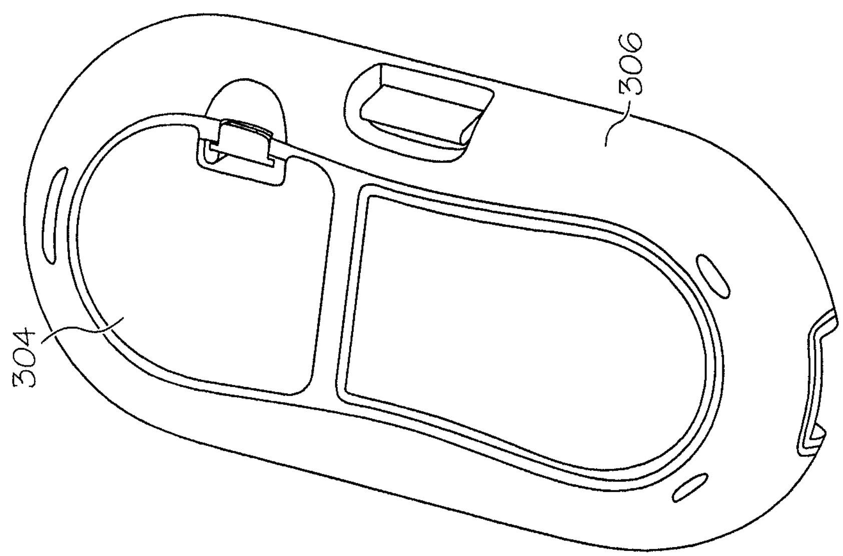
FIG. 30 is a perspective rear view of an embodiment of a diagnostic medical device.

FIGS. 30 and 31 illustrate another embodiment of a compartment 300 with a locking feature (generally designated as element 302) that inhibits unintended removal of the power supply 138 from the compartment 300, even when a panel 304 is removed. FIG. 31 illustrates the compartment 300 with the panel 304 removed. A rear housing 306 includes an insertion aperture 308 that is sized and arranged to guide the power supply 138 against spring arms (not shown in FIG. 31) thereby deflecting the spring arms. As above, the spring arms may be part of a positive contact for forming an electrical connection with the power supply 138. FIG. 31 illustrates the power supply 138 in a locked position with a first edge 310 of the power supply located under a ledge portion 312 that includes two, spaced apart ledge members 314 and 316 and a second, opposite edge 318 of the power supply located under overhang portions 320 and 322.

Figure 32:
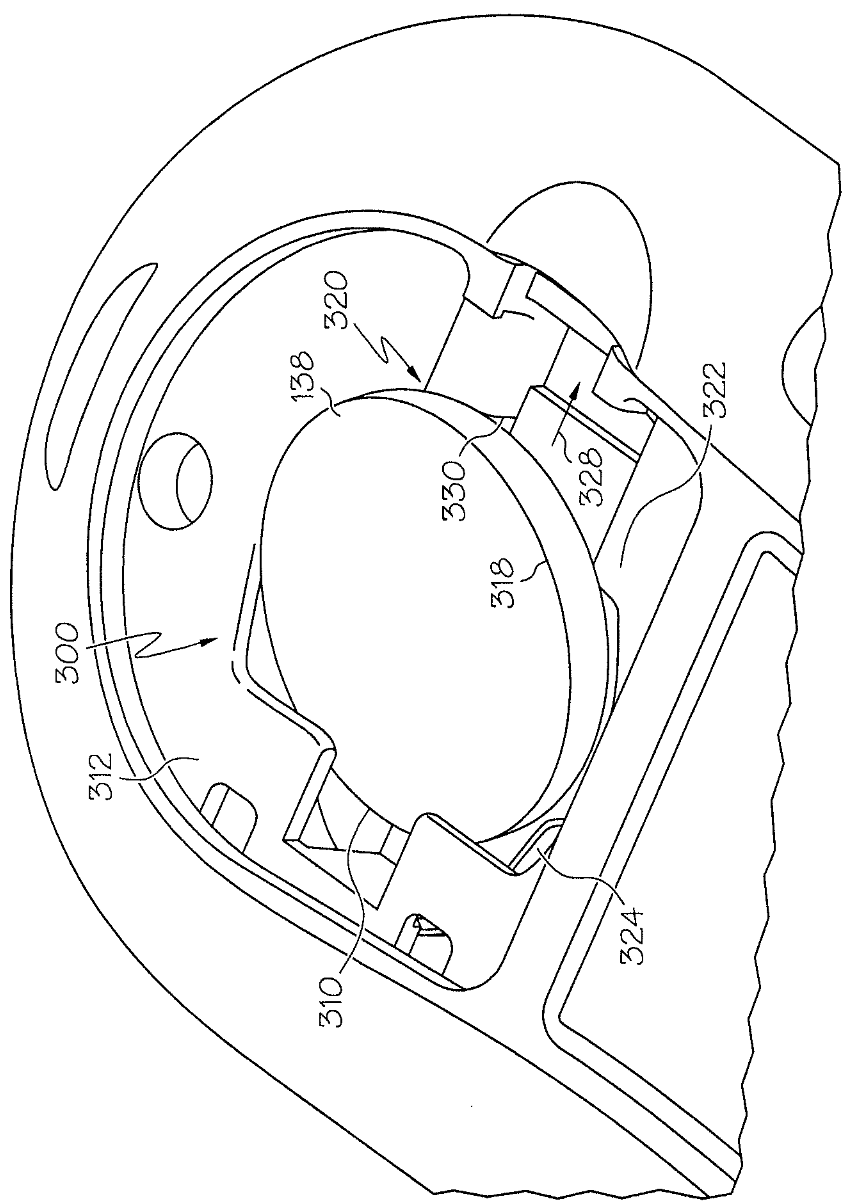
FIGS. 32 and 33 illustrate an embodiment of a process for inserting a power supply into a compartment having a locking feature.
Figure 33:
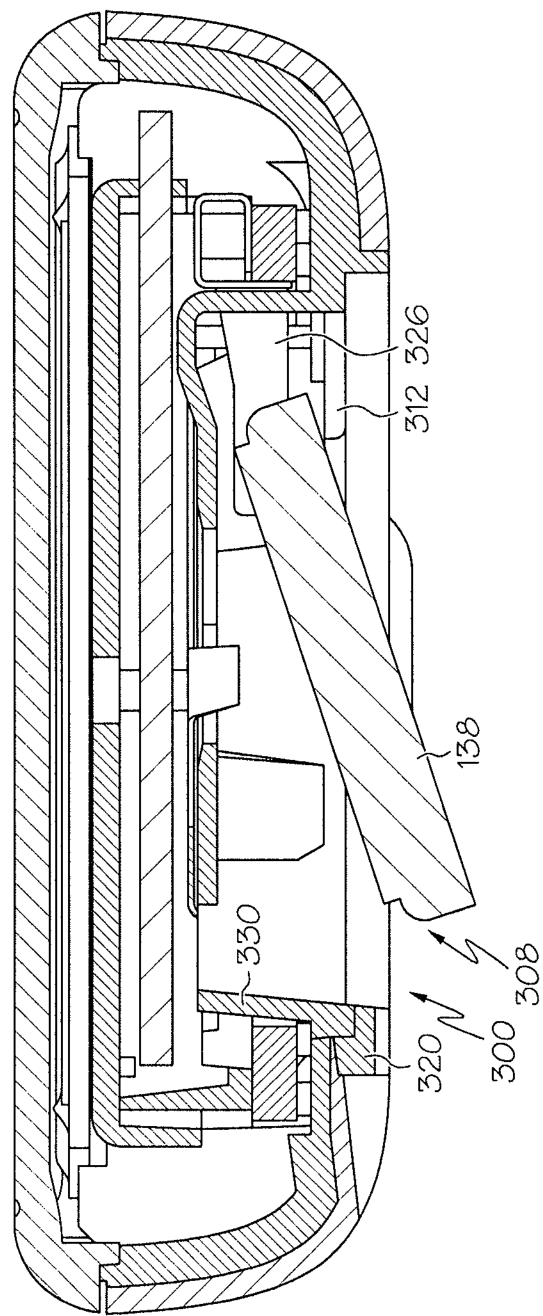

Referring to FIGS. 32 and 33, to insert the power supply 138 into the compartment 300, the edge 310 of the power supply is inserted through the insertion aperture 308 and placed beneath the ledge portion 312 to locate the power supply in an insertion position, which deflects the spring arms (only spring arm 324 is illustrated in FIG. 32 and only spring arm 326 is illustrated in FIG. 33). The spring arms 324 and 326, when deflected, provide a sufficient spring force to push the power supply 138 in the direction of the arrow 328, against a stop 330 and beneath overhanging portions 320 and 322 to the lock position without touching the power supply. To remove the power supply 138 from the compartment 300, a user applies a force to the power supply opposite arrow 328 that is sufficient for deflecting the spring arms 324 and 326 to place the power supply in the insertion position. Then, side 318 of the power supply 138 can be lifted through the insertion aperture 308 and the power supply can be removed from the compartment 300. The positive and negative contact configurations may be similar or even the same as those shown and described with reference to FIGS. 16 and 17 above.

Figure 34:
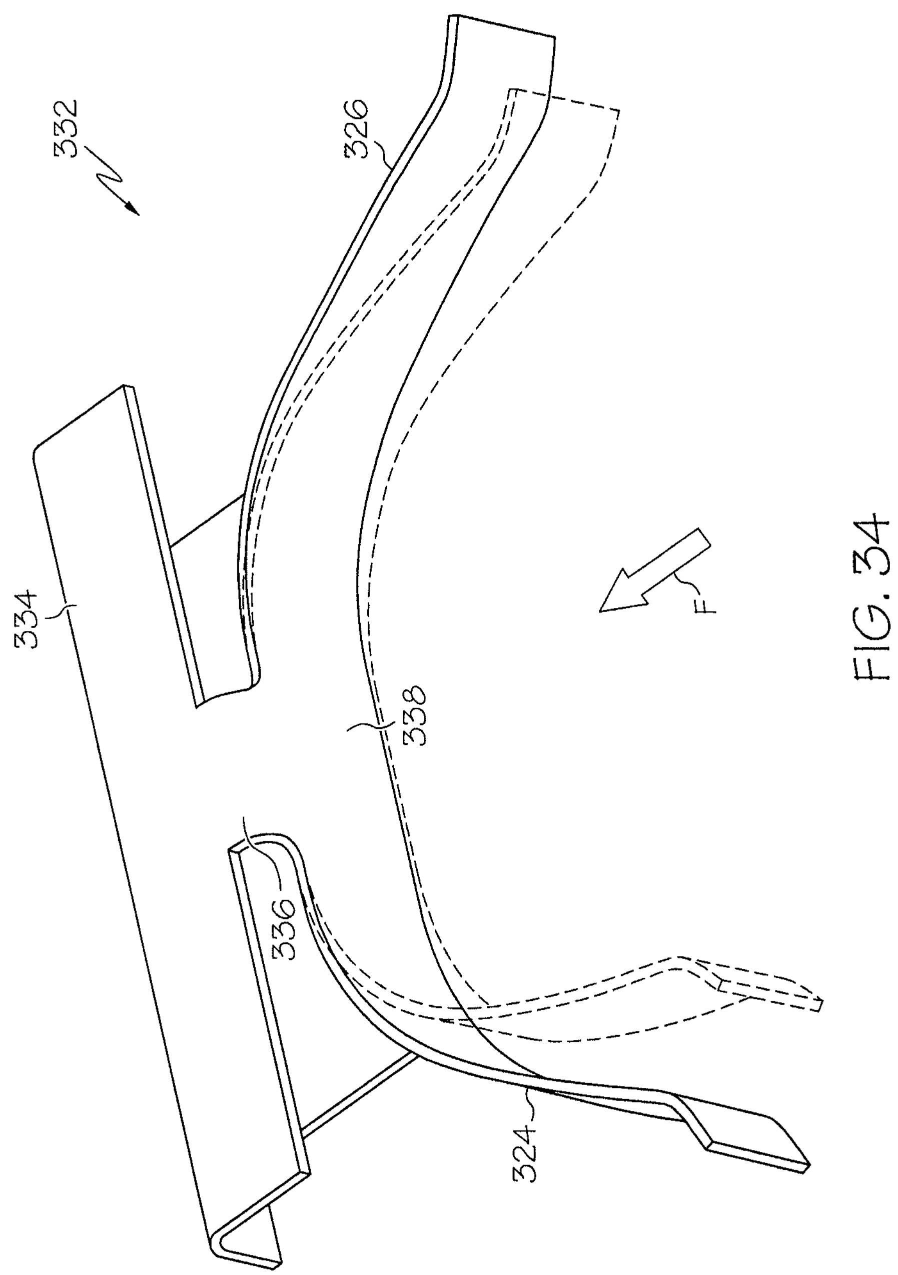
FIG. 34 is a perspective view of an embodiment of a positive contact having spring arms.

Referring to FIG. 34, a positive contact embodiment 332 is illustrated in isolation. The positive contact 332 includes a bracket portion 334 that can be connected to the main circuit board (e.g., any of the main circuit boards shown and described above) and spring arms 324 and 326 that are connected to the bracket portion by a connector 336. In one embodiment, the bracket portion 334, spring arms 324 and 326 and connector 336 are all formed of the same material (e.g., such as steel or a stainless steel alloy, such as 302 stainless steel) using any suitable process, such as stamping, bending, machining, or any combination of suitable processes. In some embodiments, the material forming the spring arms 324 and 326 may have a modulus of elasticity of about 190 GPa or more, such as about 193 GPa and a yield strength of at least about 1000 MPa, such as about 1103 MPa. In some embodiments, the spring force applied by the spring arms 324 and 326 (e.g., at their maximum deflection) may be about 1.5 N or more, such as about 2 N or more, such as about 2.35 N. In some embodiments, the maximum deflection of the spring arms 324 and 326 occurs when the power source 138 seats against an inner portion 338 of the positive contact 332 adjacent the connector 336. The degree of deflection of the spring arms 324 and 326 may depend on, among other things, the shape of the spring arms, the size of the power supply 138 and the amount of manual force F applied to the power supply during the insertion process.

Figure 35:
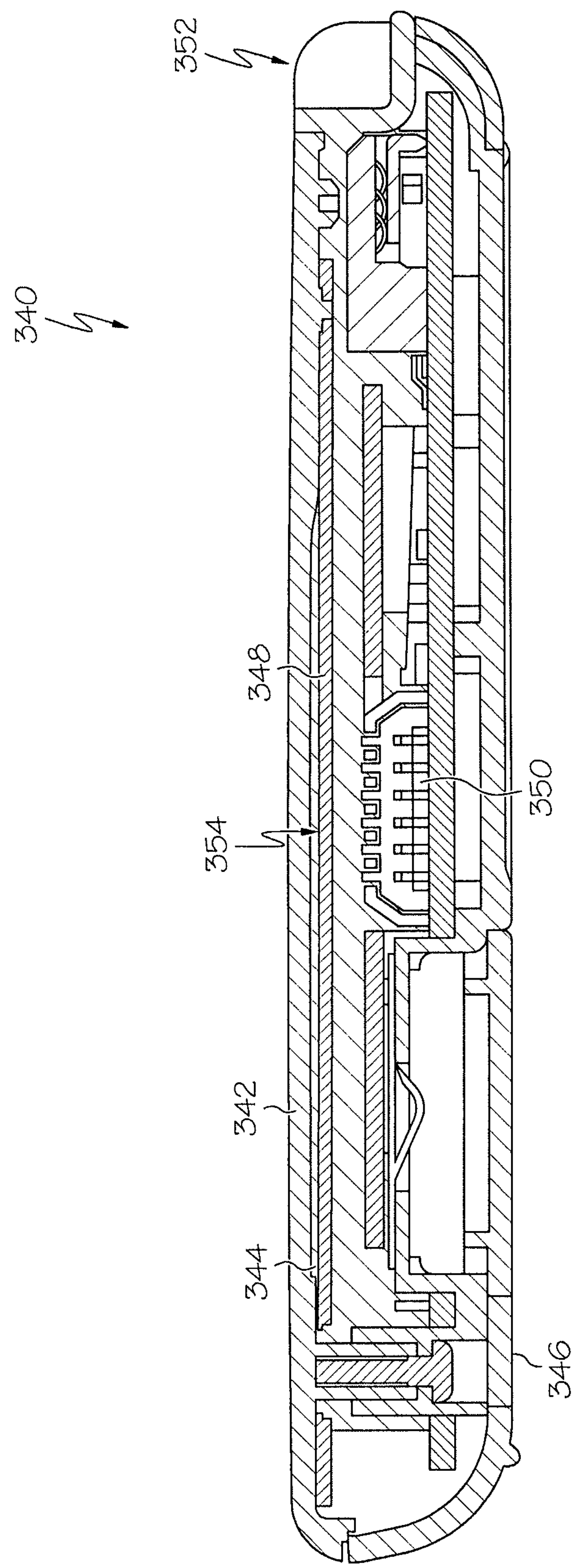
FIGS. 35-38 illustrate another embodiment of a medical diagnostic device.
Figure 36:
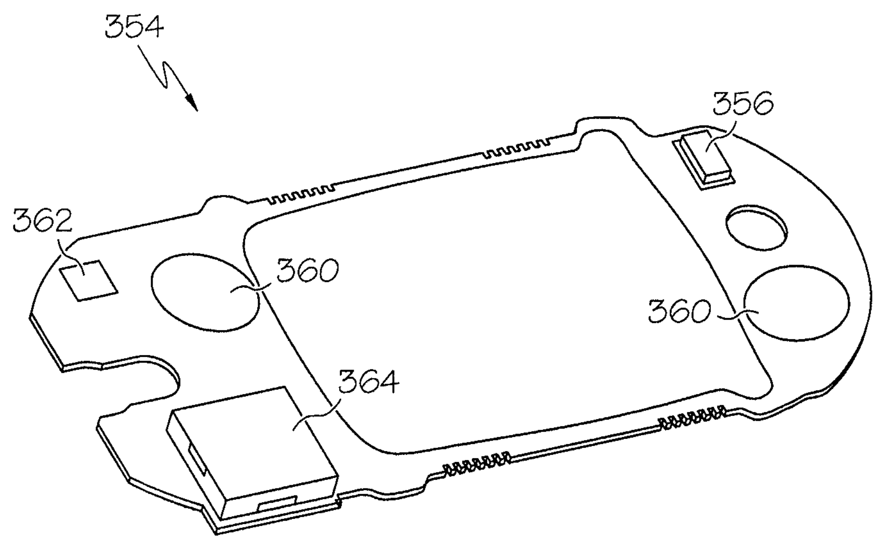
Figure 37:
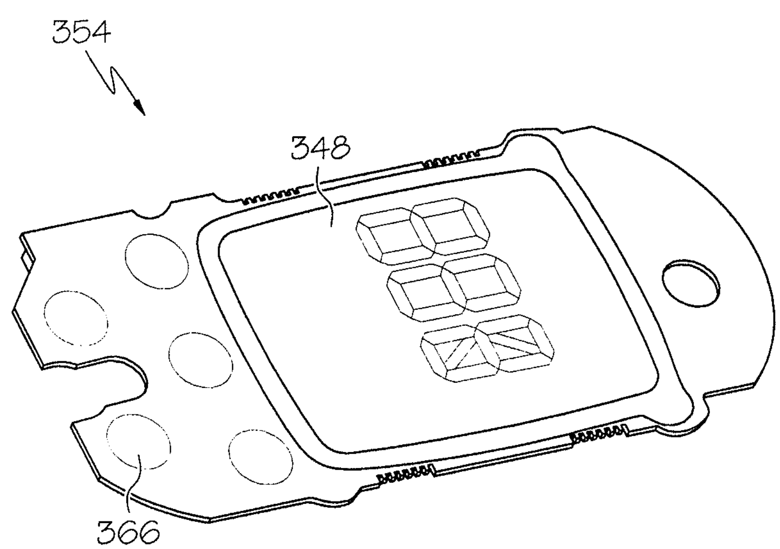

Referring now to FIG. 35, in another embodiment, a medical diagnostic device 340 has many of the features described above with regard to medical diagnostic devices 10, 100 and 274 including a protective enclosure 342 formed by a front housing 344 and a rear housing 346, a display device 348 visible through the front housing, a key card interface 350 and a strip port 352. In this embodiment, the display device 348 may be an e-paper display where the e-paper board and a touch sensor board are combined in a single display board 354. FIGS. 36 and 37 illustrate the display board 354, which includes a connector 356 that can be used to connect to a main circuit board 358, an e-paper driver controller 360 for use in controlling operation of the display device 348, a touch sensor processor 362 and an audible output device 364. As shown by FIG. 37, the e-paper display device 348 may be laminated on the display board 354 that includes touch sensor pads 366.

Figure 38:
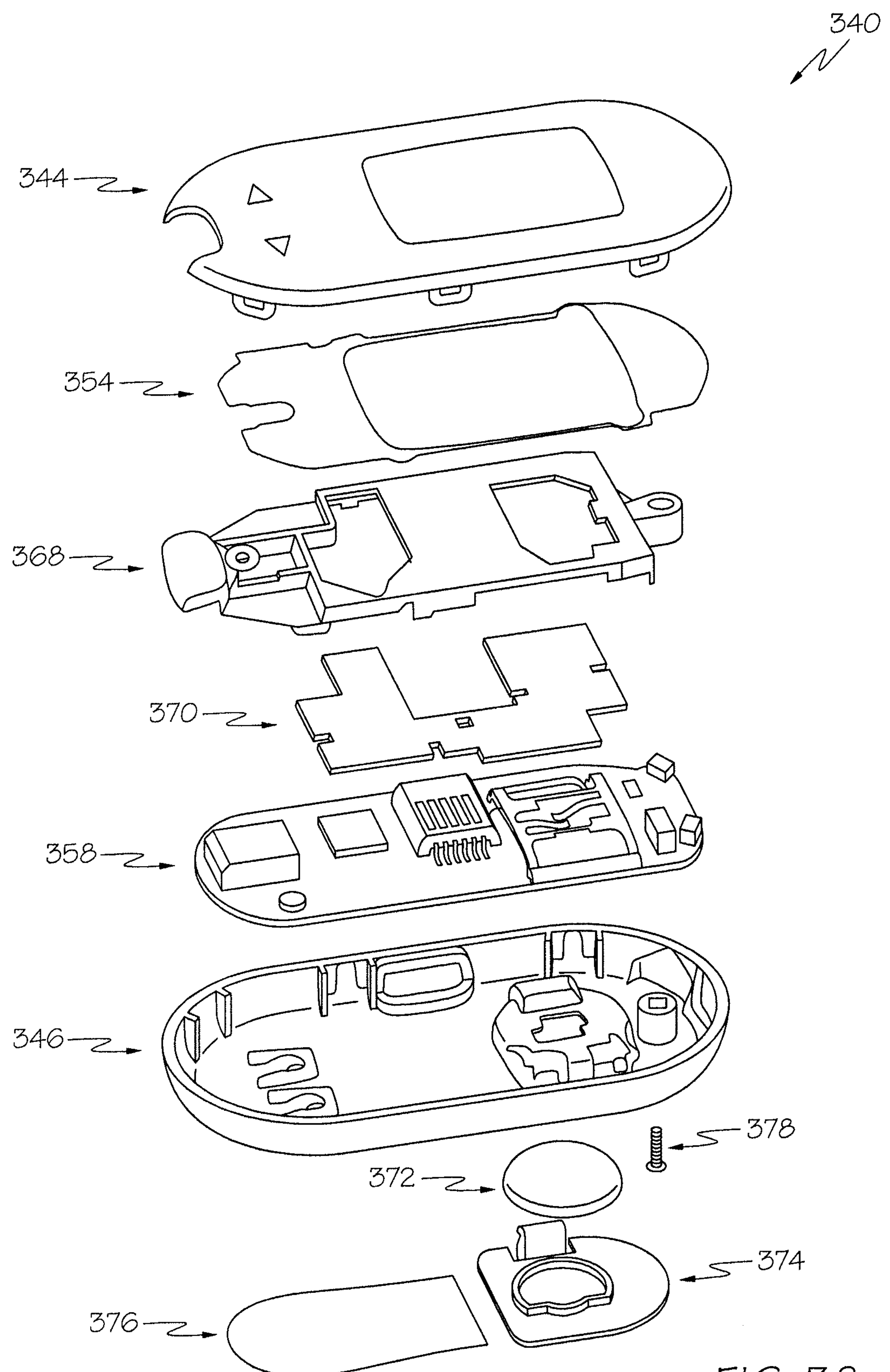

Referring to FIG. 38, an exploded view of the medical diagnostic device 340 is shown. The medical diagnostic device 340 includes the front housing 344, display board 354, frame 368, a mezzanine board 370, the main circuit board 358, rear housing 346, power supply 372, a compartment door 374, a label 376 and a fastener 378 for securing the components together.

The above-described diagnostic medical devices 10, 100, 274 and 340 may have a relatively low profile (i.e., they may be thinner) compared to other medical devices. Referring to FIG. 2, for example, the diagnostic medical device 10 may have a thickness of less than about 21 mm, such as about 15.5 mm or less. Such a reduction in thickness of the medical devices can improve their portability for a user.

The above description and drawings are only to be considered illustrative of exemplary embodiments, which achieve the features and advantages of the present invention. Modification and substitutions to specific process steps, system, and setup can be made without departing from the spirit and scope of the present invention. Accordingly, the invention is not to be considered as being limited by the foregoing description and drawings, but is only limited by the scope of the appended claims.

What is claimed is:

1. A portable handheld medical diagnostic device, comprising:

a front housing;

a rear housing opposite the front housing, the front housing and the rear housing forming a protective enclosure;

a main circuit board having printed circuits connecting electronic components located in the protective enclosure, the main circuit board including a controller facilitating a physiologic measurement;

an electronic paper display device laminated on a display board connected to the main circuit board that displays information related to the physiologic measurement;

touch sensors located on the display board; and a single-piece frame located in the protective enclosure that carries the display device and locates the display device adjacent the front housing such that the display device can be viewed from outside the protective enclosure, the frame being located between the front housing and the main circuit board, the frame including a strip port formed integrally therewith that is accessible from outside the protective enclosure.

2. The portable handheld medical diagnostic device of claim 1, wherein the frame and strip port are molded together.

3. The portable handheld medical diagnostic device of claim 1, wherein the main circuit board includes an opening that at least partially receives a battery located in the protective enclosure such that a portion of the battery is located at opposite sides of the main circuit board.

4. The portable handheld medical diagnostic device of claim 3 further comprising a battery contact comprising a spring arm arranged and configured to move the battery from an insertion position to a lock position.

5. The portable handheld medical diagnostic device of claim 4, wherein movement of the battery from the insertion position to the lock position moves the battery beneath overhang structure.

6. The portable handheld medical diagnostic device of claim 1, wherein the frame is sized and configured to align the strip port with a strip reader carried by the main circuit board.

7. The portable handheld medical diagnostic device of claim 1 further comprising an audio component carried by the frame.

8. The portable handheld medical diagnostic device of claim 1 further comprising a wireless communication board carried by the frame, the wireless communication board configured to connect to an external device.

9. The portable handheld medical diagnostic device of claim 1 wherein the touch sensors comprise, a button formed by a deflectable component mounted within an opening through the front housing, the deflectable component configured to move relative to the front housing; and a button actuation assembly located within the protective enclosure, the button actuation assembly including a membrane that spans the opening.

10. The portable handheld medical device of claim 9, wherein the deflectable component is formed of a material that is harder than material forming the membrane.

11. The portable handheld medical diagnostic device of claim 1, wherein the display device comprises a capacitive overlay configured for use in detecting user contact.

12. The portable handheld medical diagnostic device of claim 1, wherein the physiologic measurement is a blood glucose measurement.

13. The portable handheld medical diagnostic device of claim 1, wherein the strip port includes a gap that is sized to receive a test strip, the gap being located below the frame and aligned with a strip reader carried by the main circuit board.

* * * * *